(12) United States Patent
Kuboi et al.

(10) Patent No.: US 8,845,913 B2
(45) Date of Patent: *Sep. 30, 2014

(54) ION RADIATION DAMAGE PREDICTION METHOD, ION RADIATION DAMAGE SIMULATOR, ION RADIATION APPARATUS AND ION RADIATION METHOD

(71) Applicant: Sony Corporation, Tokyo (JP)

(72) Inventors: Nobuyuki Kuboi, Tokyo (JP); Shoji Kobayashi, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/012,035

(22) Filed: Aug. 28, 2013

(65) Prior Publication Data

US 2013/0344339 A1  Dec. 26, 2013

Related U.S. Application Data

(63) Continuation of application No. 12/656,830, filed on Feb. 17, 2010, now Pat. No. 8,545,710.

(30) Foreign Application Priority Data

Mar. 30, 2009  (JP) ................................. 2009-081098

(51) Int. Cl.
| | |
|---|---|
| G01R 31/00 | (2006.01) |
| B44C 1/22 | (2006.01) |
| H01J 37/302 | (2006.01) |
| C23C 14/48 | (2006.01) |
| C23C 14/54 | (2006.01) |
| G01N 23/00 | (2006.01) |
| H01L 21/3213 | (2006.01) |

(52) U.S. Cl.
CPC ............ *G01N 23/00* (2013.01); *H01J 37/3023* (2013.01); *H01L 21/32137* (2013.01); *C23C 14/48* (2013.01); *C23C 14/54* (2013.01)
USPC ................... 216/59; 216/61; 216/62; 216/66; 700/121

(58) Field of Classification Search
USPC ........................................ 216/59, 61, 62, 66
See application file for complete search history.

(56) References Cited

U.S. PATENT DOCUMENTS

| | | |
|---|---|---|
| 6,657,192 B1 | 12/2003 | Kim et al. |
| 7,972,944 B2 | 7/2011 | Kusaka et al. |

(Continued)

FOREIGN PATENT DOCUMENTS

JP  07-115071  5/1995

OTHER PUBLICATIONS

H. Ohta, et al., "Classical Interatomic Potentials for Si—O—F and Si—O—Ci Systems," Journal of Chemical Physics, vol. 115, No. 14, pp. 6679-6690, Japan.

(Continued)

*Primary Examiner* — Binh X Tran
(74) *Attorney, Agent, or Firm* — Rader, Fishman & Grauer PLLC

(57) ABSTRACT

An ion radiation damage prediction method includes a parameter computation step of computing the incidence energy and incidence angle of an incident ion hitting a fabricated object, and a step of searching for data in databases created in advance on the basis of the computed incidence energy and angle, the databases storing distributions of quantities of crystalline defects having an effect on the fabricated object, ion reflection probabilities and ion penetration depths. The method also includes finding the penetration depth and location of the incident ion based on the data found in the searching step and based on the computed incidence energy and angle, and computing a quantity of defects in the fabricated object from the penetration depth and location. A distribution of defects may be computed by performing the aforementioned steps for many incident ions.

13 Claims, 18 Drawing Sheets

(56) References Cited

U.S. PATENT DOCUMENTS

| | | |
|---|---|---|
| 8,545,710 B2 * | 10/2013 | Kuboi et al. .................... 216/59 |
| 2004/0119025 A1 | 6/2004 | Klepper et al. |
| 2006/0126046 A1 * | 6/2006 | Hansen ........................... 355/55 |
| 2008/0042060 A1 | 2/2008 | Nakasuji et al. |
| 2008/0201117 A1 * | 8/2008 | Wong et al. ....................... 703/2 |
| 2008/0308729 A1 | 12/2008 | Kimba et al. |
| 2009/0144691 A1 * | 6/2009 | Rathsack et al. ................ 716/19 |
| 2011/0020960 A1 | 1/2011 | Henry et al. |

OTHER PUBLICATIONS

J. F. Ziegler, et al., "The Stopping and Range of Ions in Solids," Pergamon Press, pp. 8-1 to 9-41, New York 1985.

* cited by examiner

FIG. 3
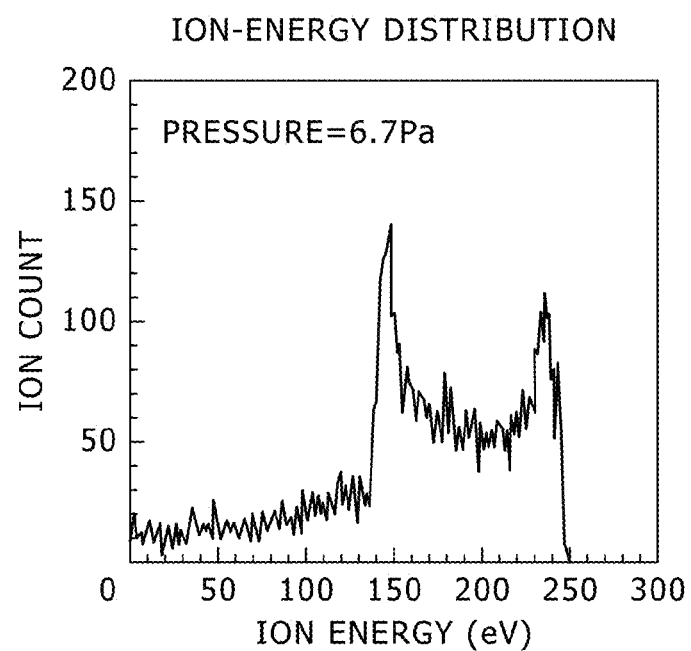
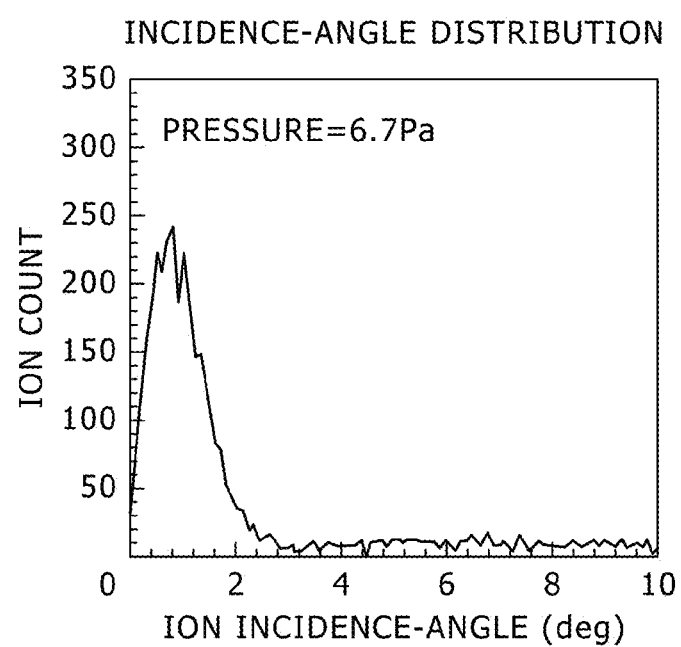

FIG.4

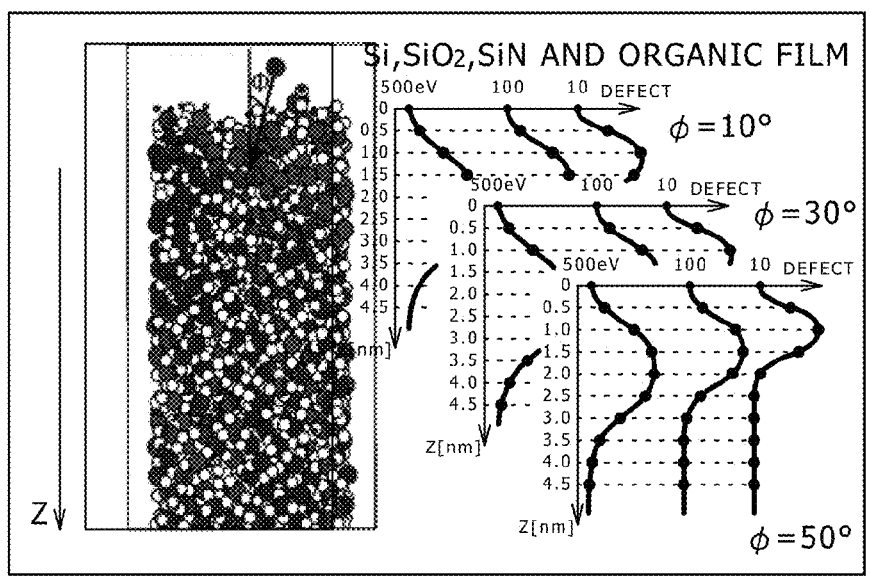

| FILM TYPE 1 OF FABEICATED OBJECT |||||||
|---|---|---|---|---|---|---|
| ION TYPE 1 |||||||
| | INCIDENCE ANGLE $\phi a$ ||| INCIDENCE ANGLE $\phi b$ |||
| ENERGY | CRYSTALLINE DEFECT | REFLECTION PROBABILITY | WEIGHT | CRYSTALLINE DEFECT | REFLECTION PROBABILITY | WEIGHT |
| E1 | D1a(z) | P1a | F1a(z) | D1b(z) | P1b | F1b(z) |
| E2 | D2a(z) | P2a | F2a(z) | D2b(z) | P2b | F2b(z) |
| E3 | D3a(z) | P3a | F3a(z) | D3b(z) | P3b | F3b(z) |
| ION TYPE 2 |||||||
| | INCIDENCE ANGLE $\phi a$ ||| INCIDENCE ANGLE $\phi b$ |||
| ENERGY | CRYSTALLINE DEFECT | REFLECTION PROBABILITY | WEIGHT | CRYSTALLINE DEFECT | REFLECTION PROBABILITY | WEIGHT |
| E1 | D1a'(z) | P1a' | F1a'(z) | D1b'(z) | P1b' | F1b'(z) |
| E2 | D2a'(z) | P2a' | F2a'(z) | D2b'(z) | P2b' | F2b'(z) |
| E3 | D3a'(z) | P3a' | F3a'(z) | D3b'(z) | P3b' | F3b'(z) |

INTERPOLATION BASED ON ENERGIES
FOR DEFFERENT INCIDENCE ANGLES φ

COMPUTE DAMAGE DISTRIBUTION
FOR A DESIRED INCIDENCE ANGLE
BY INTERPOLATION

A WEIGHTED RANDOM NUMBER
IS GENERATED TO DETERMINE
A PENETRATION DEPTH

F I G . 7
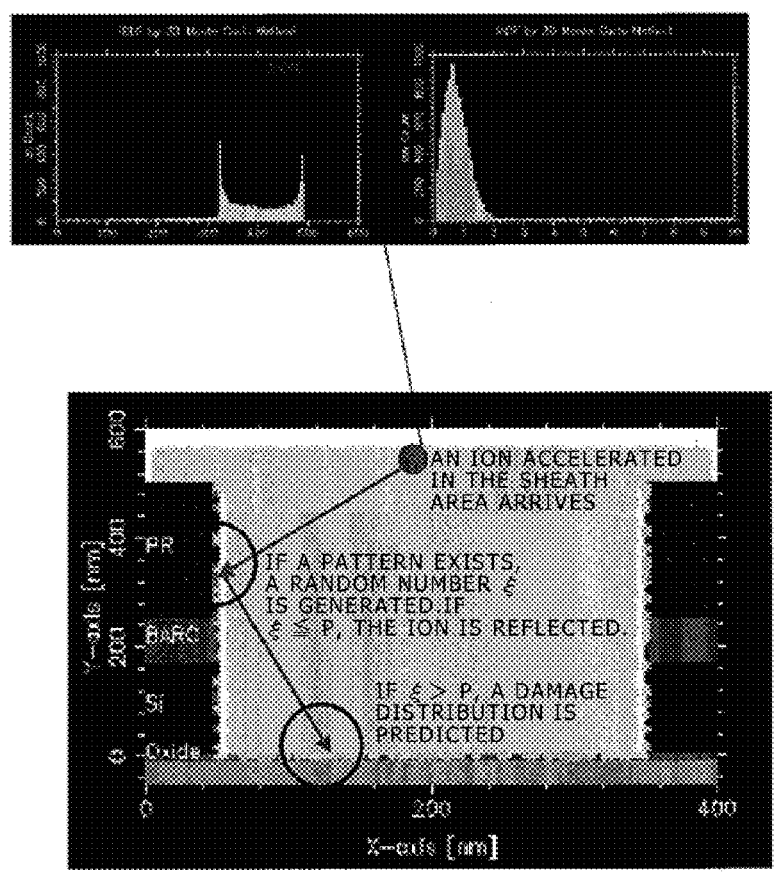

ION RADIATION DAMAGE PREDICTION METHOD, ION RADIATION DAMAGE SIMULATOR, ION RADIATION APPARATUS AND ION RADIATION METHOD

CROSS REFERENCES TO RELATED APPLICATIONS

This is a Continuation Application of the U.S. patent application Ser. No.: 12/656,830, filed Feb. 17, 2010, now U.S. Pat. No. 8,545,710 B2, which claims priority from Japanese Patent Application No. 2009-081098 filed in the Japanese Patent Office on Mar. 30, 2009, the entire content of which are incorporated herein by reference.

BACKGROUND OF THE INVENTION

1. Field of the Invention

The present invention relates to an ion radiation damage prediction method, an ion radiation damage simulator, an ion radiation apparatus and an ion radiation method.

2. Description of the Related Art

Results of studies have indicated that it is quite within the bounds of possibility that damages caused by incoming ions generated in processing such as an etching process, a physical vapor deposition (PVD) process or an ion injection process to a fabricated film have a big effect on electrical characteristics of the device including the film. Such damages are thus a problem that needs to be solved as quickly as possible. A typical damage caused by incoming ions incident to a processed film serving as a target film of a process generating the ions is a crystalline defect. Thus, the target film including a pattern means a film hit by ions.

By merely making use of the contemporary measurement apparatus, however, it is difficult to conduct a direct analysis on a damage given to a real pattern (particularly, the side wall of the pattern). It is thus important to predict such a damage given to a film hit by incident ions by simulation in order to study details of relations between the damage and electrical characteristics of the device including the film as well as details of a measure that needs to be taken for improving the electrical characteristics.

For example, in a simulation of the existing ion implantation process or a stopping and range of ions in matter (SRIM) simulation, it is possible to predict the depth of penetration of incident ions into a target film which is assumed to have an amorphous structure. It is to be noted that for more information on the simulation of the existing ion implantation process, the reader is suggested to refer to documents such as Japanese Patent Laid-open No. Hei 7-115071 whereas for more information on the SRIM simulation, the reader is suggested to refer to documents such as "The stopping and Range of Ions in Solids," J. F. Ziegler, J. P. Biersack and U. Littmark, Pergamon Press, New York, 1985.

However, a crystalline defect caused by the penetration of incident ions as a defect of the target film cannot be expressed quantitatively by taking the crystal structure of the target film into consideration. Typical examples of the crystalline defect are a disarray in the lattice crystal of the polysilicon and/or the silicon oxide.

In addition, a damage simulation process making use of the existing molecular dynamics simulator is carried out by considering interactions between incident ions penetrating a target film and atoms composing the target film. As a result, even in the case of a crystal-lattice disarray caused by energies of incoming ions, incidence angles of the incoming ions and the type of the target film can be predicted at an atomic level or a molecular level. It is to be noted that for more information on this simulation process, the reader is suggested to refer to documents such as H. Ohta and Hamaguchi, "Classical interatomic potentials for Si—O—F and Si—O—Cl systems," Journal of Chemical Physics, Vol. 115, number 14, pp. 6679-6690, 2001.

Within a realistic time period of a computation that can be carried out by a computer such as one incorporated in an ordinary manufacturing apparatus, however, it is possible to compute only a distribution of damages in a very small limited area having typical dimensions of several nm×several nm. A typical example of the realistic time period of computation that can be carried out by a computer is several weeks. Due to limitations imposed by such a very small limited area, however, the actual computation carried out in accordance with molecular dynamics is applicable to cases not more than the case of an assumed planar target film which ignores created patterns. In addition, in the case of incoming ions each having a small mass (for example, hydrogen ion), the flying distance inside the target film increases. Thus, the time it takes to carry out the computation becomes even longer.

It is thus absolutely necessary to provide a new computation algorithm in which results of computation carried out to find a distribution of damages caused by radiation of ions in a real pattern having a scale of 100 nm and in an actual process of such a scale are fed back to the device process development within a short realistic time period such as several hours or several days. A distribution of damages is computed by for example predicting a distribution of crystalline defects and/or verifying a defect generation mechanism.

In addition, an ion radiation apparatus capable of correcting a process condition in order to reduce the number of damages by adopting the new computation algorithm described above becomes necessary for developments of high-performance of image sensors. Typical examples of the ion radiation apparatus are a dry etching apparatus and an ion injection apparatus.

SUMMARY OF THE INVENTION

A problem to be solved by the present invention is the fact that, even though a crystal-lattice disarray caused by energies of incoming ions, incidence angles of the incoming ions and the type of the target film can be predicted at an atomic level or a molecular level, if the prediction must be carried out within a realistic time period of a computation that can be carried out by a computer such as one incorporated in an ordinary manufacturing apparatus, it is possible to compute only a distribution of damages in a very small limited rectangular area having typical dimensions of several nm×several nm.

Inventors of the present invention have innovated a new technique for feeding back results of computation carried out to find a distribution of damages caused by radiation of ions in a real pattern having a scale of 100 nm and in an actual process of such a scale to development of a device process within a short realistic time period such as several hours or several days.

An ion radiation damage prediction method according to an embodiment of the present invention, includes a parameter computation step of computing the collision position of an incident ion hitting a fabricated object and the incidence angle of the incident ion by consideration of a transport path traced by the incident ion as a path to the fabricated object and by adoption of the Monte Carlo method which takes a distribution of flux quantities of incident ions, a distribution of incidence energies of incident ions and a distribution of incidence angles of incident ions as input parameters, and a defect-distribution computation step. The defect-distribution computation step carries out a search operation to search for data by referring to the information found at the parameter computation step as well as databases created in advance by computation according to classical molecular dynamics or the first principle of molecular dynamics to serve as a database used for storing a distribution of quantities of crystalline defects having an effect on the fabricated object, a database used for storing a distribution of ion reflection probabilities and a database used for storing a distribution of ion penetration depths. Further, the defect-distribution computation step finds the penetration depth of the incident ion hitting the fabricated object and the penetration location of the incident ion on the basis of the data found in the search operation, the incidence energy of the incident ion hitting the fabricated object and the incidence angle of the incident ion. In addition, the defect-distribution computation step computes a distribution of defects caused by radiation of ions in the fabricated object from the penetration depth of the incident ion hitting the fabricated object and the penetration location of the incident ion.

In accordance with the ion radiation damage prediction method provided by the present invention as described above, it is possible to quantitatively predict a distribution of incident-ion penetrations into the side wall of a fabricated object and/or the bottom of the fabricated object and a 2-dimensional or 3-dimensional distribution of physical damage quantities (or crystalline defects) caused by incident ions within a realistic period of computation time. It is to be noted that, by merely carrying out experiments, it is difficult to measure the distributions within a realistic period of measurement time. It is possible to quantitatively predict the distributions within a realistic period of computation time because of the use of the databases which have been created in advance by computation according to molecular dynamics, whereby less time is required for computing a distribution of ion penetration depths and a distribution of quantities of crystalline defects.

An ion radiation damage simulator according to another embodiment of the present invention includes a processing section configured to carry out computation to predict defects generated in a fabricated object due to incident ions radiated to the fabricated object, and an output section configured to output a distribution of the defects computed by the processing section as the defects generated in the fabricated object due to incident ions radiated to the fabricated object. The processing section carries out the computation by executing a parameter computation step of computing the collision position of an incident ion hitting a fabricated object and the incidence angle of the incident ion by consideration of a transport path traced by the incident ion as a path to the fabricated object and by adoption of the Monte Carlo method which takes a distribution of flux quantities of incident ions, a distribution of incidence energies of incident ions and a distribution of incidence angles of incident ions as input parameters. The processing section carries out the computation by further executing a defect-distribution computation step including a step of carrying out a search operation to search for data by referring to the information found at the parameter computation step as well as databases created in advance by computation according to classical molecular dynamics or the first principle of molecular dynamics to serve as a database used for storing a distribution of quantities of crystalline defects having an effect on the fabricated object, a database used for storing a distribution of ion reflection probabilities and a database used for storing a distribution of ion penetration depths. The defect-distribution computation step further includes a step of finding the penetration depth of the incident ion hitting the fabricated object and the penetration location of the incident ion on the basis of the data found in the search operation, the incidence energy of the incident ion hitting the fabricated object and the incidence angle of the incident ion. The defect-distribution computation step further includes a step of computing a distribution of defects caused by radiation of ions in the fabricated object from the penetration depth of the incident ion hitting the fabricated object and the penetration location of the incident ion.

By making use of the ion radiation damage simulator provided by the present embodiment as described above, it is possible to quantitatively predict a distribution of incident-ion penetrations into the side wall of a fabricated object and/or the bottom of the fabricated object and a 2-dimensional or 3-dimensional distribution of physical damage quantities (or crystalline defects) caused by incident ions within a realistic period of computation time. It is to be noted that, by merely carrying out experiments, it is difficult to measure the distributions within a realistic period of measurement time. It is possible to quantitatively predict the distributions within a realistic period of computation time because of the use of the databases which have been created in advance by computation according to molecular dynamics, whereby less time is required for computing a distribution of ion penetration depths and a distribution of quantities of crystalline defects.

An ion radiation apparatus according to a further embodiment of the present invention includes a shape simulator configured to predict a change caused by an etching process as a change of the shape of a fabricated object serving as a subject of the etching process. The ion radiation apparatus further includes an ion radiation damage simulator configured to predict an ion radiation damage generated by the etching process in the fabricated object by referring to shape data predicted by the shape simulator as shape data of the fabricated object. The ion radiation apparatus further includes a control section configured to execute control to produce an etching condition, which allows the number of aforementioned ion radiation damages to be minimized, on the basis of a simulation result predicted by the ion radiation damage simulator. The ion radiation apparatus further includes an etching process section configured to carry out the etching process on the fabricated object in accordance with a command received from the control section. The ion radiation damage simulator includes a processing section configured to carry out computation to predict defects generated in a fabricated object due to incident ions radiated to the fabricated object, and an output section configured to output a distribution of the defects computed by the processing section as the defects generated in the fabricated object due to incident ions radiated to the fabricated object. The processing section carries out the computation by executing a parameter computation step of computing the collision position of an incident ion hitting a fabricated object and the incidence angle of the incident ion by consideration of a transport path traced by the incident ion as a path to the fabricated object and by adoption of the Monte Carlo method which takes a distribution of flux quantities of incident ions, a distribution of incidence energies of incident ions and a distribution of incidence angles of incident ions as input parameters. The processing section carries out the computation by further executing a defect-distribution computation step including a step of carrying out a search operation to search for data by referring to the information found at the parameter computation step as well as databases created in advance by computation according to classical molecular dynamics or the first principle of molecular dynamics to serve as a database used for storing a distribution of quantities of crystalline defects having an effect on the fabricated object, a database used for storing a distribution of ion reflection probabilities and a database used for storing a distribution of ion penetration depths. The defect-distribution computation step further includes a step of finding the penetration depth of the incident ion hitting the fabricated object and the penetration location of the incident ion on the basis of the data found in the search operation, the incidence energy of the incident ion hitting the fabricated object and the incidence angle of the incident ion. The defect-distribution computation step further includes a step of computing a distribution of defects caused by radiation of ions in the fabricated object from the penetration depth of the incident ion hitting the fabricated object and the penetration location of the incident ion.

By making use of the ion radiation apparatus provided by the present embodiment as described above, it is possible to quantitatively predict a distribution of incident-ion penetrations into the side wall of a fabricated object and/or the bottom of the fabricated object and a 2-dimensional or 3-dimensional distribution of physical damage quantities (or crystalline defects) caused by incident ions within a realistic period of computation time. It is to be noted that, by merely carrying out experiments, it is difficult to measure the distributions within a realistic period of measurement time. It is possible to quantitatively predict the distributions within a realistic period of computation time because of the use of the databases which have been created in advance by computation according to molecular dynamics, whereby less time is required for computing a distribution of ion penetration depths and a distribution of quantities of crystalline defects.

An ion radiation apparatus according to a still further embodiment of the present invention includes an ion radiation damage simulator configured to predict a damage generated in a fabricated object by ions radiated to the fabricated object serving as a subject of an ion-injection process. The ion radiation apparatus further includes a control section configured to execute control to produce an ion injection condition included in a range of process conditions as an injection condition, which allows the number of aforementioned ion-radiation damages to be minimized, on the basis of a simulation result predicted by the ion radiation damage simulator. The ion radiation apparatus further includes an ion-injection process section configured to carry out the ion-injection process on the fabricated object in accordance with a command received from the control section. The ion radiation damage simulator includes a processing section configured to carry out computation to predict defects generated in a fabricated object due to incident ions radiated to the fabricated object, and an output section configured to output a distribution of the defects computed by the processing section as the defects generated in the fabricated object due to incident ions radiated to the fabricated object. The processing section carries out the computation by executing a parameter computation step of computing the collision position of an incident ion hitting a fabricated object and the incidence angle of the incident ion by consideration of a transport path traced by the incident ion as a path to the fabricated object and by adoption of the Monte Carlo method which takes the film type of the fabricated object hit by the incident ions, the structure of the fabricated object, a distribution of flux quantities of incident ions, a distribution of incidence energies of incident ions and a distribution of incidence angles of incident ions as input parameters. The processing section carries out the computation by further executing a defect-distribution computation step including a step of carrying out a search operation to search for data by referring to the information found at the parameter computation step as well as databases created in advance by computation according to classical molecular dynamics or the first principle of molecular dynamics to serve as a database used for storing a distribution of quantities of crystalline defects having an effect on the fabricated object, a database used for storing a distribution of ion reflection probabilities and a database used for storing a distribution of ion penetration depths. The defect-distribution computation step further includes a step of finding the penetration depth of the incident ion hitting the fabricated object and the penetration location of the incident ion on the basis of the data found in the search operation, the incidence energy of the incident ion hitting the fabricated object and the incidence angle of the incident ion. The defect-distribution computation step further includes a step of computing a distribution of defects caused by radiation of ions in the fabricated object from the penetration depth of the incident ion hitting the fabricated object and the penetration location of the incident ion.

By making use of the ion radiation apparatus provided by the present embodiment as described above, it is possible to quantitatively predict a distribution of incident-ion penetrations into the side wall of a fabricated object and/or the bottom of the fabricated object and a 2-dimensional or 3-dimensional distribution of physical damage quantities (or crystalline defects) caused by incident ions within a realistic period of computation time. It is to be noted that, by merely carrying out experiments, it is difficult to measure the distributions within a realistic period of measurement time. It is possible to quantitatively predict the distributions within a realistic period of computation time because of the use of the databases which have been created in advance by computation according to molecular dynamics, whereby less time is required for computing a distribution of ion penetration depths and a distribution of quantities of crystalline defects.

An ion radiation method according to a yet further embodiment of the present invention includes a process of carrying out shape simulation to predict a change caused by an etching process as a change of the shape of a fabricated object serving as a subject of the etching process. The ion radiation method further includes a process of carrying out ion radiation damage simulation to predict an ion radiation damage generated by the etching process in the fabricated object by referring to shape data predicted by execution of the shape simulation as shape data of the fabricated object. The ion radiation method further includes a process of executing control to produce an etching condition, which allows the number of aforementioned ion radiation damages to be minimized, on the basis of a simulation result predicted by carrying out the ion radiation damage simulation. The ion radiation method further includes a process of carrying out the etching process on the fabricated object in accordance with the etching condition. The ion radiation damage simulation is carried out by executing a parameter computation step of computing the collision position of an incident ion hitting a fabricated object and the incidence angle of the incident ion by consideration of a transport path traced by the incident ion as a path to the fabricated object and by adoption of the Monte Carlo method which takes a distribution of flux quantities of incident ions, a distribution of incidence energies of incident ions and a distribution of incidence angles of incident ions as input parameters. The ion radiation damage simulation is carried out by further executing a defect-distribution computation step including a step of carrying out a search operation to search for data by referring to the information found at the parameter computation step as well as databases created in advance by computation according to classical molecular dynamics or the first principle of molecular dynamics to serve as a database used for storing a distribution of quantities of crystalline defects having an effect on the fabricated object, a database used for storing a distribution of ion reflection probabilities and a database used for storing a distribution of ion penetration depths. The defect-distribution computation step further includes a step of finding the penetration depth of the incident ion hitting the fabricated object and the penetration location of the incident ion on the basis of the data found in the search operation, the incidence energy of the incident ion hitting the fabricated object and the incidence angle of the incident ion. The defect-distribution computation step further includes a step of computing a distribution of defects caused by radiation of ions in the fabricated object from the penetration depth of the incident ion hitting the fabricated object and the penetration location of the incident ion.

By making use of the ion radiation method provided by the present embodiment as described above, it is possible to quantitatively predict a distribution of incident-ion penetrations into the side wall of a fabricated object and/or the bottom of the fabricated object and a 2-dimensional or 3-dimensional distribution of physical damage quantities (or crystalline defects) caused by incident ions within a realistic period of computation time. It is to be noted that, by merely carrying out experiments, it is difficult to measure the distributions within a realistic period of measurement time. It is possible to quantitatively predict the distributions within a realistic period of computation time because of the use of the databases which have been created in advance by computation according to molecular dynamics, whereby less time is required for computing a distribution of ion penetration depths and a distribution of quantities of crystalline defects.

An ion radiation method according to a yet further embodiment of the present invention includes a process of carrying out ion radiation damage simulation to predict a damage generated in a fabricated object by ions radiated to the fabricated object serving as a subject of an ion-injection process. The ion radiation method further includes a process of executing correction to produce a corrected ion injection condition included in a range of process conditions as an injection condition, which allows the number of aforementioned ion-radiation damages to be minimized, on the basis of a simulation result predicted by carrying out the ion radiation damage simulation. The ion radiation method further includes a process of carrying out the ion-injection process to inject ions into the fabricated object in accordance with the corrected ion injection condition. The ion radiation damage simulation is carried out by executing a parameter computation step of computing the collision position of an incident ion hitting a fabricated object and the incidence angle of the incident ion by consideration of a transport path traced by the incident ion as a path to the fabricated object and by adoption of the Monte Carlo method which takes a distribution of flux quantities of incident ions, a distribution of incidence energies of incident ions and a distribution of incidence angles of incident ions as input parameters. The ion radiation damage simulation is carried out by further executing a defect-distribution computation step including a step of carrying out a search operation to search for data by referring to the information found at the parameter computation step as well as databases created in advance by computation according to classical molecular dynamics or the first principle of molecular dynamics to serve as a database used for storing a distribution of quantities of crystalline defects having an effect on the fabricated object, a database used for storing a distribution of ion reflection probabilities and a database used for storing a distribution of ion penetration depths. The defect-distribution computation step further includes a step of finding the penetration depth of the incident ion hitting the fabricated object and the penetration location of the incident ion on the basis of the data found in the search operation, the incidence energy of the incident ion hitting the fabricated object and the incidence angle of the incident ion. The defect-distribution computation step further includes a step of computing a distribution of defects caused by radiation of ions in the fabricated object from the penetration depth of the incident ion hitting the fabricated object and the penetration location of the incident ion.

By making use of the ion radiation method provided by the present embodiment as described above, it is possible to quantitatively predict a distribution of incident-ion penetrations into the side wall of a fabricated object and/or the bottom of the fabricated object and a 2-dimensional or 3-dimensional distribution of physical damage quantities (or crystalline defects) caused by incident ions within a realistic period of computation time. It is to be noted that, by merely carrying out experiments, it is difficult to measure the distributions within a realistic period of measurement time. It is possible to quantitatively predict the distributions within a realistic period of computation time because of the use of the databases which have been created in advance by computation according to molecular dynamics, whereby less time is required for computing a distribution of ion penetration depths and a distribution of quantities of crystalline defects.

Since the ion radiation damage prediction method provided by the embodiment of the present invention allows the simulation time to be shortened considerably, the ion radiation damage prediction method offers a merit that the turn around time (TAT) of the developments of a Complementary Metal Oxide Semiconductor (CMOS) device process and an image sensor process as well as the evaluations of these processes can be shortened so that the development cost can be reduced.

Since the ion radiation damage simulator provided by the embodiment of the present invention allows the simulation time to be shortened considerably, the ion radiation damage prediction method offers a merit that the TAT of the developments of a CMOS device process and an image sensor process as well as the evaluations of these processes can be shortened so that the development cost can be reduced.

Since the ion radiation apparatus provided by the embodiments of the present invention is capable of considerably shortening the time of simulation of an etching process and ion injection process which make use of ion radiation and minimizing the number of damages caused by the ion radiation while implementing desired processing dimensions, the ion radiation apparatus offers a merit that the TAT of the developments of the etching process for a CMOS device and an image sensor as well as the evaluations of these processes can be shortened so that the development cost can be reduced.

Since the ion radiation method provided by the embodiment of the present invention is capable considerably shortening the time of simulation of an ion injection process, the ion radiation method offers a merit that the TAT of the developments of the ion injection process for a CMOS device and an image sensor as well as the evaluations of these processes can be shortened so that the development cost can be reduced.

BRIEF DESCRIPTION OF THE DRAWINGS

FIG. 3 shows a plurality of diagrams illustrating typical results of prediction carried out by making use of a sheath simulator;

FIG. 4 shows a plurality of diagrams illustrating the concept of a database;

FIG. 7 shows a plurality of explanatory diagrams to be referred to in explanation of interpolation for the case of an incident ion with an incidence energy E of 200 eV and an incidence angle φ of 40 degrees;

DETAILED DESCRIPTION OF THE PREFERRED EMBODIMENTS

Preferred embodiments each representing an implementation of the present invention will be described hereinafter.

<1. First Embodiment>
[First Typical Example of an Ion Radiation Damage Prediction Method]

Figure 1:
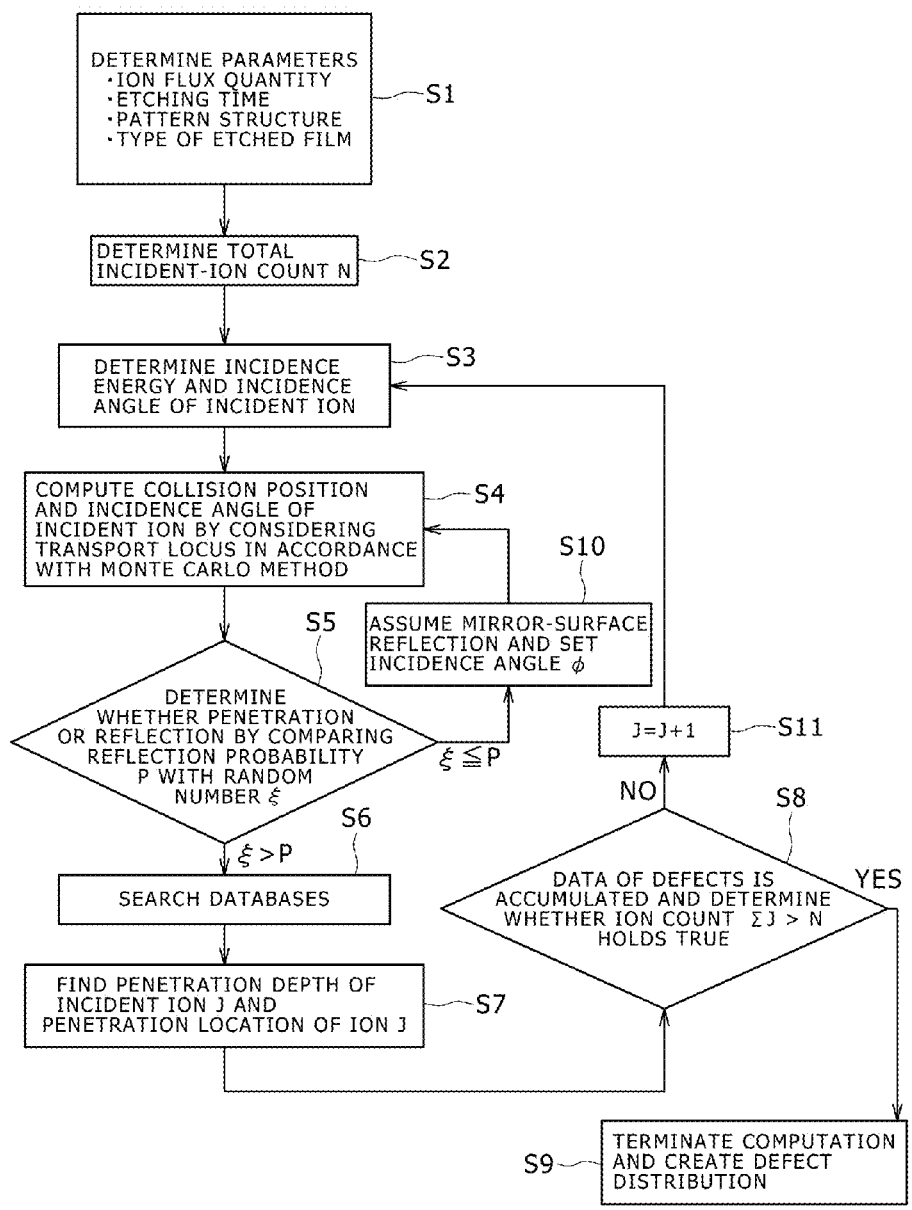
FIG. 1 shows a flowchart representing a first typical example of an ion radiation damage prediction method according to a first embodiment of the present invention.

A first typical example of an ion radiation damage prediction method according to a first embodiment of the present invention is explained by referring to a flowchart shown in FIG. 1.

As shown in the flowchart of FIG. 1, first of all, a parameter computation step is carried out. At the parameter computation step, the collision position of an incident ion incoming to a fabricated object and the incidence angle of the incident ion are computed by consideration of a transport path traced by the incident ion as a path to the fabricated object and by adoption of the Monte Carlo method which takes a distribution of flux quantities of incident ions, a distribution of incidence energies of incident ions and a distribution of incidence angles of incident ions as input parameters.

To put it more concretely, the parameter computation step is carried out as follows. At the first step S1, input parameters are determined. That is to say, the first step S1 is carried out in order to determine the input parameters such as the film type of a fabricated object hit by an incident ion, the structure of the fabricated object, the flux quantity of the incident ion and the length of an ion radiation time. The structure of a fabricated object includes the size of the fabricated object and the shape of the fabricated object.

Then, at the second step S2, a total incident-ion count N is determined. The total incident-ion count N is the total number of incoming ions incident to a fabricated object within the ion radiation time period. The second step S2 is carried out on the basis of the input parameters in accordance with the Monte Carlo method.

Then, at the third step S3, the incidence energy E of the incident ion and the incidence angle φ of the ion are found. To be more specific, the third step S3 is carried out in order to find the incidence energy E of the Jth incident ion J hitting the fabricated object and the incidence angle φ of the ion J where reference symbol J appended as a suffix to the word 'ion' indicates that the ion is the Jth incident ion.

After the parameter computation step described above has been completed, a defect-distribution computation step is carried out. At this defect-distribution computation step, first of all, data is searched for in a search operation by referring to the information found at the parameter computation step as well as databases created in advance by computation according to classical molecular dynamics or the first principle of molecular dynamics. The databases include a database used for storing a distribution of quantities of crystalline defects having an effect on the fabricated object, a database used for storing a distribution of ion reflection probabilities and a database used for storing a distribution of ion penetration depths. Then, on the basis of the data found in the search operation, the incidence energy E of the Jth incident ion J hitting the fabricated object and the incidence angle φ of the ion J, the penetration depth of the Jth incident ion J hitting the fabricated object and the penetration location of the ion are found. Finally, a distribution of defects caused by radiation of ions in the fabricated object is computed.

Figure 2:
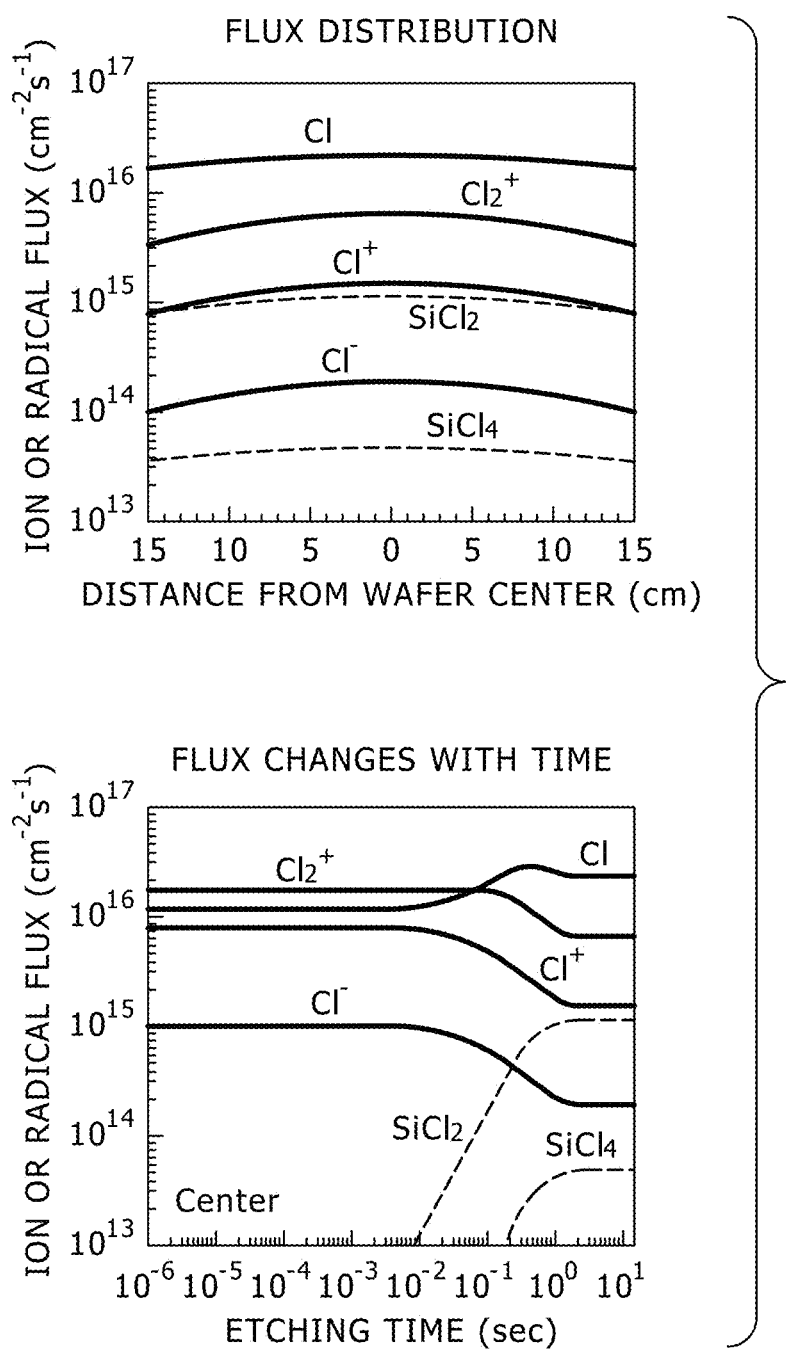
FIG. 2 shows a plurality of diagrams illustrating typical results of prediction carried out by making use of a plasma gas simulator.

As a distribution of incidence energies E and a distribution of incidence angles φ, it is possible to make use of typically prediction results produced by a plasma gas simulator and a sheath simulator which are shown in none of the figures. As described above, the incidence energy E and the incidence angle φ are used as input parameters in the operation to search a database and also in computation based on interpolation. FIG. 2 is a plurality of diagrams showing typical results of prediction carried out by making use of a plasma gas simulator. On the other hand, FIG. 3 shows a plurality of diagrams showing typical results of prediction carried out by making use of a sheath simulator. Instead of making use of prediction results produced by a plasma gas simulator and a sheath simulator, it is possible to make use of values obtained as a result of actual measurement of plasma-emitted light or actual measurement of an energy spectrum.

The aforementioned plasma gas simulator and the sheath simulator mentioned above will be described later.

To put it concretely, the defect-distribution computation step described above is carried out as follows.

First of all, a transport locus of the incident ion J into the fabricated object is taken into consideration in computing the collision position of an incident ion J and the incidence angle of the ion J in accordance with the Monte Carlo method at the fourth step S4. To put it in detail, at this fourth S4, the transport locus traced by an incident ion J as a locus to a fabricated object is found for the shape of the fabricated object by adoption of the Monte Carlo method. For example, the fourth step S4 is carried out in order to compute the position of collision between the incident ion J and the surface of the fabricated object as well as the incidence angle formed by the transport path of the incident ion J in conjunction with the surface of the fabricated object.

In addition, for incidence of every ion having an incidence energy E and an incidence angle $\phi$ at the surface of the fabricated object, data such as a crystalline defect D, an ion reflection probability P and a weight value F is computed in advance. It is to be noted that each of the crystalline defect D and the weight value F is a function of z where reference symbol z denotes the depth of the ion penetration. The data such as a crystalline defect D, an ion reflection probability P and a weight value F has been computed by making use of a simulator according to classical molecular dynamics or the first principle of molecular dynamics typically for a fabricated object having a planar shape. Then, results of the computation are stored as a database in advance. That is to say, the results of the computation are typically used for creating a database as shown in conceptual diagrams of FIG. 4.

The crystalline defect D(z) computed by making use of a simulator of molecular dynamics as a defect caused by one incident ion is defined in definition (1) or (2) given as follows.

Figure 5:
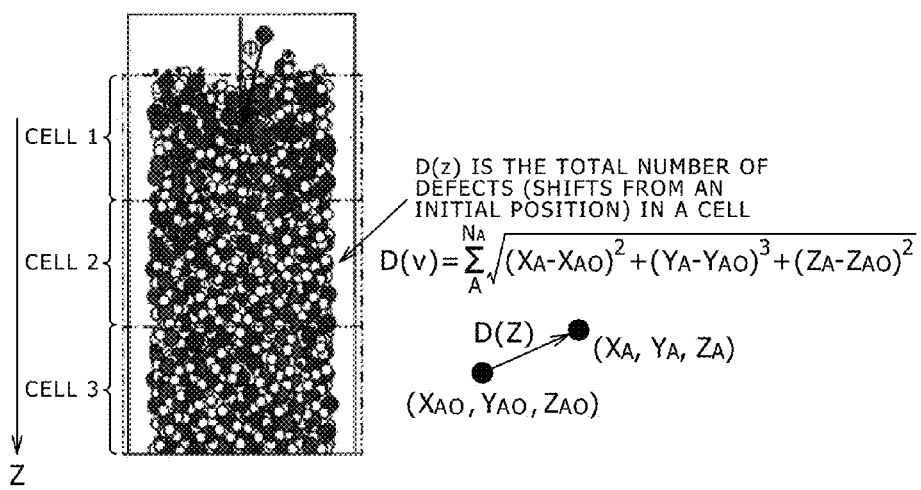
FIG. 5 is a diagram showing a computation area of computation according to molecular dynamics.

(1) Definition of the Crystalline Defect D Computed in Accordance with Classical Molecular Dynamics The area of computation making use of a simulator according to classical molecular dynamics is divided into cells as shown in a diagram of FIG. 5. To be more specific, the area of computation is typically divided into cell 1, cell 2 and cell 3 which each have a size of 2 nm×2 nm×2 nm. As is obvious from Eq. (1) given below, the crystalline defect D(z) in a cell is defined as the sum of each shift of the position $(X_A, Y_A, Z_A)$ of an atom A existing at a depth z from the initial crystal structure position $(X_{AO}, Y_{AO}, Z_{AO})$. Reference symbol $N_A$ used in the equation denotes the number of crystal atoms which exist in one cell.

$$D(z) = \sum_{A}^{NA} \sqrt{(X_A - X_{AO})^2 + (Y_A - Y_{AO})^2 + (Z_A - Z_{AO})^2} \quad (1)$$

(2) Definition of the Crystalline Defect D Computed in Accordance with the First Principle Molecular Dynamics In accordance with the first principle molecular dynamics, it is possible to compute the state of a molecule or an atom as a function of wave. The defect D(zi) is defined as the sum of binding energy variations $\Delta U$ in a cell. The binding energy variations $\Delta U$ are each expressed by the equation $\Delta U = U/U0$ and summed to define the defect D(zi). Reference symbol U denotes a covalent binding energy which is expressed by the following equation:

$$U = \int E \times n(E) dE$$

As is obvious from the above equation, the covalent binding energy U is estimated from the atomic state n (E). Reference notation E used in the above equation denotes a Hamiltonian diagonalized component. On the other hand, reference symbol U0 used in the equation $\Delta U = U/U0$ denotes a covalent binding energy for a case of no ion injection.

With the crystalline defect D defined in accordance with the definitions described above, a total damage $D_T(zi)$ finally accumulated in cell i is defined by Eq. (2) as follows:

$$D_T(zi) = \sum^{Ni} D(z) \quad (2)$$

Reference notation Ni used in Eq. (2) given above denotes the number of incident ions injected into cell i.

In addition, there are computation methods A and B used for determining the transport locus of an incident ion at the fourth step. The computation methods A and B are explained as follows.

Computation method A is a method for computing the transport locus of an incident ion by assuming that the ion propagates by repeating direct advancing and mirror-surface reflection (or penetration into a film) in a fabricated object such as a pattern.

Computation method B is a method for computing the transport locus of an incident ion by considering also an electric-potential effect (also referred to as an electrical charging effect) due to an electric-charge distribution caused by an etching fabrication process as a distribution of electric charges on the surface of a pattern.

In accordance with computation method (A), a transport locus is expressed in terms of gradients Vy/Vx obtained from a distribution of ion-speed components (Vx, Vy) and straight lines obtained from a radiation position (or an opposite position).

In accordance with computation method (B), on the other hand, it is necessary to consider the existence of an electron in addition to an ion, compute an electric-potential distribution and an electric-field distribution which are created by the electron and the ion in the pattern and solve motion equations of the ion and the electron which are propagating through the distribution of electric potentials and the distribution of electric fields. The motion equations are solved in the same way as a process of solving Poisson equations by adoption of typically a successive method such as the successive over relaxation (SOR) method. For details, the reader is suggested to refer to documents such as a doctoral thesis authored by Taku Shimada with a title of "Development Modeling of a Trench Shape of $SiO_2$ and an Organic Low-Permittivity Material in a Surface Charging/Etching/Deposition Competition Process" and submitted to Keio University in 2006.

Then, the fifth step S5 is carried out to determine whether the incident ion J experiences penetration or reflection in accordance with a result of comparing a reflection probability P with a random number $\xi$. That is to say, at the fifth step S5, the reflection probability P found by referring to the incidence energy E of the incident ion J and the incidence angle $\phi$ of the incident ion J is compared with the random number $\xi$ in order to determine whether the incident ion J penetrates into the fabricated object or the incident ion J is reflected by the surface of the fabricated object.

For example, when an incident ion J collides with the side wall of a pattern serving as a fabricated object or the bottom of the pattern, a random number $\xi$ having a value in the range $0<\xi<1$ is generated at that point. In addition, the incidence energy E and the incidence angle $\phi$ of the incident ion J are retrieved from a database and then used in a spline interpolation process to find a reflection probability P. Subsequently, the random number $\xi$ is compared with the reflection probability P in order to produce a result of determination as to whether the incident ion J penetrates the portion of the pattern serving as the fabricated object to a depth z and gives rise to a crystalline defect or the incident ion J is reflected by the surface of the pattern in a mirror-reflection phenomenon and keeps the energy of the incident ion J.

If the determination result produced at the fifth step S5 shows that the reflection probability P is smaller than the random number that is $\xi$, the relation $\xi>P$ holds true to indicate that the incident ion J has penetrated the fabricated object, the following steps are carried out. At the sixth step S6, a database is searched for data such as the film type of the fabricated object and the type of the incident ion J. The database is used for storing a distribution of incident ions in the fabricated object. The distribution of incident ions in the fabricated object has been created in advance by calculation according to classical molecular dynamics and calculation according to the first principle of molecular dynamics on the basis of the incidence energy E of the incident ion J, the incidence angle $\phi$ of the ion and the film type of the fabricated object.

Then, at the seventh step S7, the penetration depth of the incident ion J and the penetration location of the incident ion J are found. To put it in detail, at the seventh step S7, on the basis of the data found in the search operation carried out at the sixth step S6, the incidence energy E and the incidence angle $\phi$ of the incident ion J, the penetration depth of the incident ion J and the penetration location of the ion J are found.

Thus, a distribution of crystalline defects caused by an incident ion J having an incidence energy E and an incidence angle $\phi$ in a cell can be found. It is to be noted that the distribution of crystalline defects is a distribution with respect to the penetration depth z. In addition, a weighted random number is generated to and used for determining the penetration depth z. It is to be noted that the weighted random number is a product of a random number and a weight F(z) representing an ion-count distribution rate at the penetration depth z where the ion-count distribution rate is the ratio of an incident-ion count to a total incident-ion count used in the calculation according to molecular dynamics.

Figure 6A:
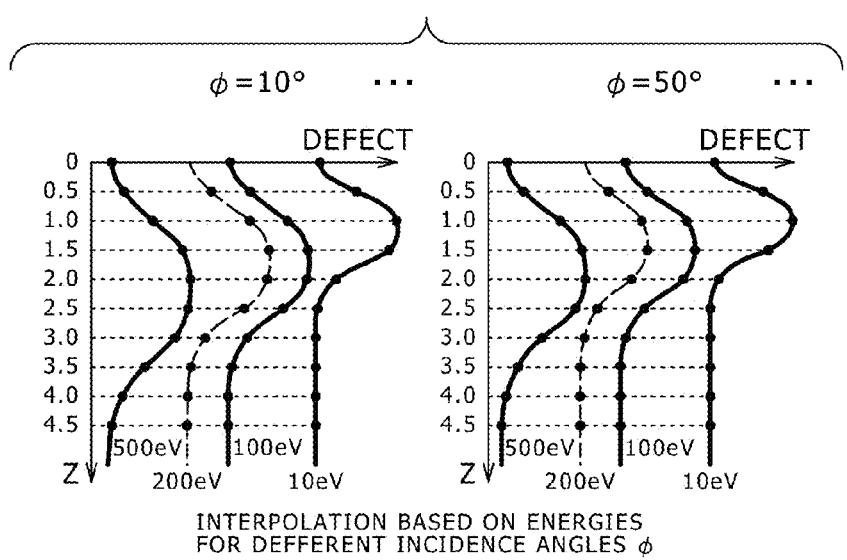
FIGS. 6A to 6C are a plurality of diagrams to be referred to in explanation of defect distributions, interpolation based on the defect distributions, computation of a damage distribution by the interpolation, generation of a weighted random number and determination of a depth based on the random number from the damage distribution found by the interpolation.
Figure 6B:
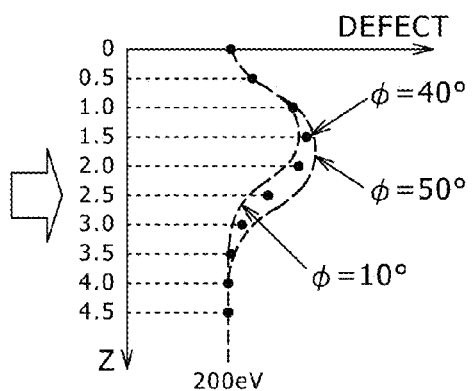
Figure 6C:
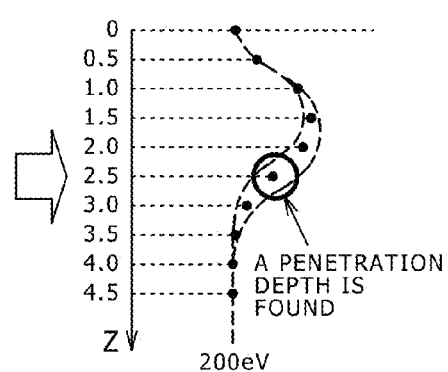

For example, for $\xi>P$ representing a case in which a crystalline defect is generated, the database is searched for the film type of the fabricated object and the type of the incident ion J. Crystalline-defect distribution curves shown in FIG. 6A are used in a spline interpolation process to find a crystalline-defect distribution curve for an incidence energy E and an incidence angle $\phi$ as shown in the diagram of FIG. 6B. Then, a weighted random number is generated and used for determining a penetration depth z on the basis of the crystalline-defect distribution curve found by the spline interpolation process as shown in the diagram of FIG. 6C. As an example, FIG. 7 is a plurality of explanatory diagrams showing a spline interpolation process for the case of an incident ion J with an incidence energy E of 200 eV and an incidence angle $\phi$ of 40 degrees.

Then, at the eighth step S8, data of defects is accumulated and an ion count $\Sigma J$ of the accumulated data of defects is compared with the total incident-ion count N in order to determine whether or not the relation $\Sigma J > N$ holds true. To put it in detail, data of defects is accumulated by storing the penetration depth z of the incident ion J and the penetration location of the ion J. In addition, the ion count $\Sigma J$ representing the number of processed incident ions J is compared with the total incident-ion count N in order to determine whether or not the number of incident ions J has reached the total incident-ion count N.

If the determination result produced at the eighth step S8 indicates that the number of processed incident ions J has not reached the total incident-ion count N, the flow goes on to an eleventh step S11 at which the index J is updated by incrementing the index J by 1 as expressed by the equation J=J+1 in the flowchart shown in FIG. 1. Then, the flow goes back to the third step S3 in order to repeat the processing for the incident ion indicated by the updated index J (=J+1).

As a matter of fact, the sequence of steps ranging from the third step S3 to the eighth step S8 is carried out repeatedly till the number of processed incident ions J reaches the total incident-ion count N.

If the determination result produced at the eighth step S8 indicates that the number of processed incident ions J has reached the total incident-ion count N, on the other hand, the flow goes on to the ninth step S9 at which the ion radiation damage prediction method is terminated and a crystalline-defect distribution is created on the basis of the accumulated data of the crystalline defects.

In addition, if the determination result produced at the fifth step S5 shows that the reflection probability P is equal to or greater than the random number that is $\xi$, the relation $\xi \leq P$ holds true to indicate that the incident ion J is reflected by the surface of the fabricated object, on the other hand, the flow goes on to the tenth step S10 at which the incident ion is determined to have experienced mirror-surface reflection and the incidence angle $\phi$ of the ion is found. That is to say, at the tenth step S10, the incident ion is determined to have experienced a mirror-surface reflection process of reflecting the ion from the surface of the fabricated object, and the incidence angle $\phi$ of the ion is determined. Then, the flow goes back to the fourth step S4.

As described above, in accordance with the algorithm, the processing from the third step S3 to the eleventh step S11 is carried out repeatedly for each Jth incident ion identified by the index J having a value which satisfies the relations $1 \leq J \leq N$.

The ion radiation damage prediction method described above is characterized in that, the transport path recognized in accordance with the Monte Carlo method as a path traced by an incident ion (or an incident particle) in the fabricated object (or pattern) is taken into consideration whereas the databases created in advance by computation according to molecular dynamics are used. Thus, it is possible to substantially decrease the length of the portion of the time allocated to the computation according to molecular dynamics. In addition, it is also possible to compute a 2-dimensional or 3-dimensional distribution of defects caused by incident ions in the side wall and/or bottom of a fabricated object (or a pattern) created in a 100 nm process within a short period of time. It is to be noted that it was so far difficult to compute the 2-dimensional or 3-dimensional distribution within a short period of time.

Provided for each type of the incident ion, each energy of the incident ion, each incidence angle of the incident ion and each type of the film hit by the incident ion, the databases serving as the subject of the search operation typically include a database used for storing a distribution of quantities of crystalline defects generated on the film serving as a subject of ion radiation, a database used for storing a distribution of ion reflection probabilities, a database of distributions of ion penetration depths and a database of weight values.

In accordance with the ion radiation damage prediction method described above, it is possible to quantitatively predict a distribution of incident-ion penetrations into the side wall and/or bottom of a fabricated object and a 2-dimensional or 3-dimensional distribution of physical damage quantities (or crystalline defects) caused by incident ions within a realistic period of computation time. It is to be noted that, by merely carrying out experiments, it is difficult to measure the distributions within a realistic period of measurement time. The above predict is possible because of the use of the databases created in advance by computation according to molecular dynamics, whereby less time is required for computing a distribution of ion penetration depths and a distribution of quantities of crystalline defects.

For example, the algorithm adopted by the ion radiation damage prediction method makes it possible to carry out computation for a real pattern having a scale of 100 nm. It is to be noted that the computation for a real pattern having a scale of 100 nm is difficult to carry out as calculation according to molecular dynamics. Thus, the distribution of crystalline defects D can be found at a speed higher then that of the existing calculation according to molecular dynamics. It is worth noting that the distribution of crystalline defects D is information indicating how far crystalline defects D are generated in the real pattern.

In addition, the ion radiation damage prediction method can be applied not only to crystalline defects caused by incident ions, but also to for example crystalline defects generated by photons such as UV (ultraviolet) light in a film serving as the subject of an etching fabrication process.

On top of that, by making use of a shape simulator to predict a state in which the shape of a fabricated object (or a pattern) is changing due to processing such as an etching fabrication process, it is possible to predict a distribution of ion damages in a real manner for the fabricated object (or a pattern) changing the shape thereof. Thus, it is possible to provide optimum process conditions which takes both the shape specifications and defects caused by ion damages. It is to be noted that the defects caused by ion damages are considered to be defects relevant to the electrical characteristics of the device which is being fabricated.

The shape simulator will be described later.

[Typical Sheath Simulators]

A sheath simulator is used for a prediction process in accordance with the Monte Carlo method. In the prediction process carried out by the sheath simulator, ions having velocities according to the Maxwell distribution are radiated to a sheath area in which each of the ions is accelerated by a difference in electric potential between the ion and the sheath area and collides with a neutral particle existing in the sheath area. Each of the ions repeats the acceleration and the collision.

Figure 8:
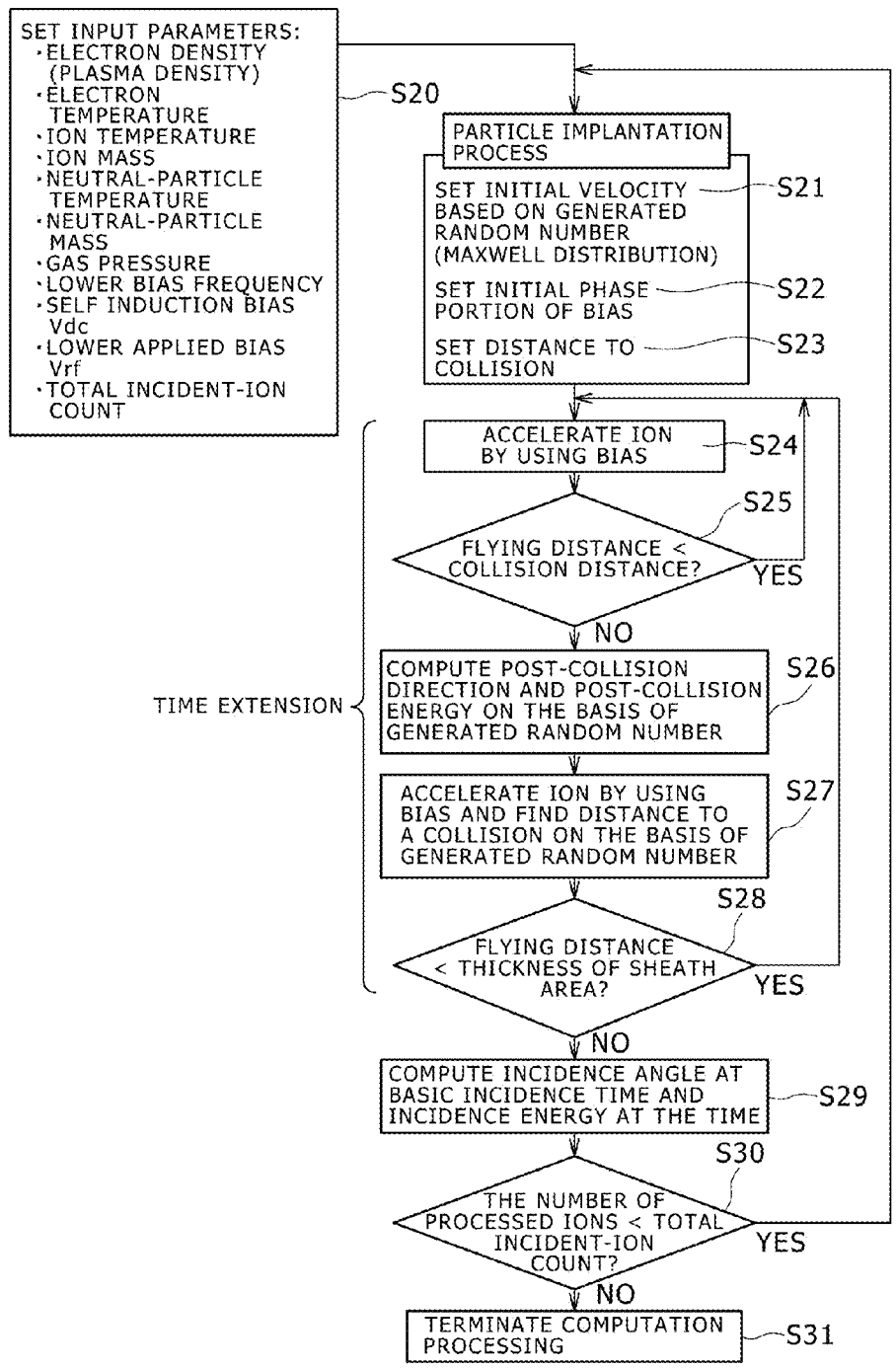
FIG. 8 shows a flowchart representing processing carried out by a sheath simulator to predict a distribution of ion energies and a distribution of ion incidence angles in accordance with the first embodiment of the present invention.

FIG. 8 shows a flowchart representing processing carried out by the sheath simulator.

As shown in FIG. 8, the flowchart begins with a step S20 which is an input-parameter setting process of setting input parameters. The input parameters include an electron density or a plasma density, an electron temperature, an ion temperature, an ion mass, a neutral-particle temperature, a neutral-particle mass, a gas pressure, a lower bias frequency, a self induction bias Vdc, lower applied bias Vrf and the number of incident ions.

After the input-parameter setting step, a particle implantation process is carried out by execution of a step S21 of setting an initial velocity, a step S22 of setting an initial phase portion of a bias and a step S23 of setting a distance to a collision.

To put it in detail, first of all, at the step S21, the initial velocity of an ion is set on the basis of a generated random number. For example, the initial velocity of the ion is given in accordance with the Maxwell distribution.

Then, at the step S22, an initial phase portion of a bias is set on the basis of a generated random number. Subsequently, at the step S23, a distance to a collision with the fabricated object is set on the basis of a generated random number.

Then, a step S24 is carried out as a bias acceleration step. That is to say, at the bias acceleration step, the ion is accelerated by applying the bias to the ion.

Subsequently, a step S25 is carried out as a flying distance and collision distance comparison step. At step S25, if 'the flying distance<the collision distance' holds true to indicate that the flying distance is shorter than the distance to a collision with the fabricated object, the flow goes back to the step S24 at which the ion is accelerated by applying the bias to the ion.

If the relation of 'the flying distance≥the collision distance' holds true to indicate that the flying distance is equal to or longer than the distance to a collision with the fabricated object, on the other hand, the flow goes on to a step S26 at which the post-collision direction of the ion and the post-collision energy of the ion are computed on the basis of a generated random number. For example, the step S26 is carried out in order to compute the post-collision penetration direction taken by the incident ion as the penetration direction after the collision between the ion and the fabricated object or the post-collision reflection direction taken by the incident ion as the reflection direction following the collision between the ion and the fabricated object on the basis of a generated random number. In addition, the post-collision energy of the ion is also computed on the basis of the generated random number.

Then, a step S27 is carried out in order to accelerate the incident ion by applying a bias to the ion and find a distance to a collision on the basis of a generated random number. That is to say, the incident ion is accelerated by a bias applied to the ion and a distance to a collision between the ion and the surface of the fabricated object is computed on the basis of a generated random number.

Subsequently, a step S28 is carried out as a flying distance and sheath-area thickness comparison step. At step S28, if 'the flying distance<the thickness of the sheath area' holds true to indicate that the flying distance is shorter than the thickness of the sheath area, the flow goes back to the step S24 at which the ion is accelerated by applying the bias to the ion.

If the relation of 'the flying distance≥the thickness of the sheath area' holds true to indicate that the flying distance is equal to or longer than the thickness of the sheath area, on the other hand, the flow goes on to a step S29 at which the incidence angle at the basic incidence time and the incidence energy at the basic incidence time are computed. For example, before entering the sheath area, the ion has a velocity according to the Maxwell distribution as described above. The ion having a velocity according to the Maxwell distribution then enters the sheath area. When the ion enters the sheath area, the sheath area accelerates the ion due to a difference in electric potential between the ion and the sheath area. While the ion is being accelerated, the ion also collides with a neutral particle. The repetition of the acceleration and the repetition of the collision are computed by adoption of typically the Monte Carlo method.

Next, a step S30 is carried out as a step of producing a result of determination as to whether or not the number of processed particles is smaller than a set particle count representing the number of particles. If the determination result produced at the step S30 indicates that the relation of 'the number of processed particles<the set particle count' meaning that the number of processed particles is smaller than the set particle count holds true, the flow goes back to the particle implantation process which starts with the step S21.

If the result of the determination indicates that the relation of 'the number of processed particles≥the set particle count' holds true, on the other hand, the flow of the prediction processing goes on to a step S31 at which the computation/prediction processing is terminated.

The sheath simulator carries out computation based on the algorithm described above in order to predict behaviors of incident ions in a sheath area.

[Second Typical Example of the Ion Radiation Damage Prediction Method]

Figure 9:
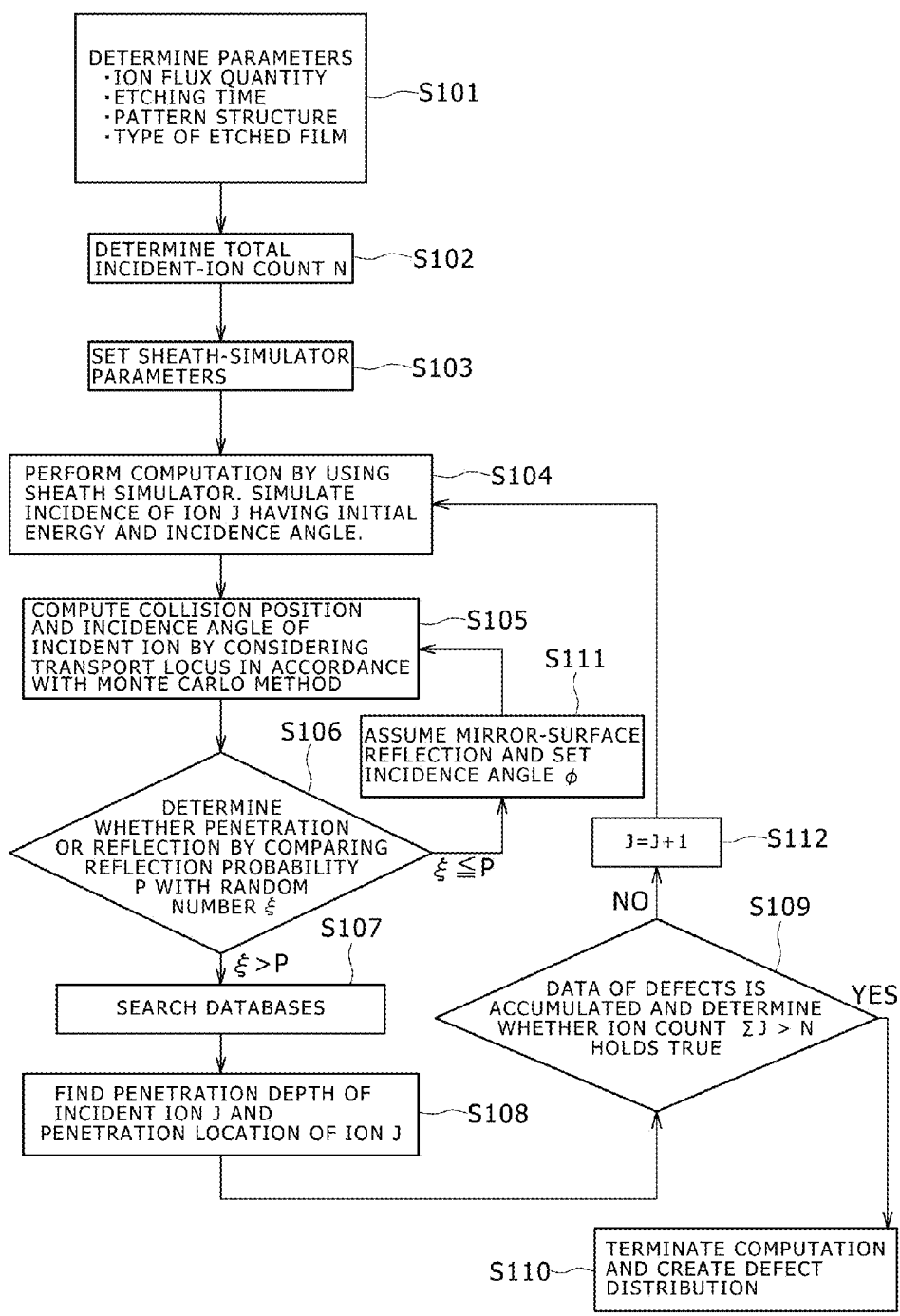
FIG. 9 shows a flowchart representing a second typical example of the ion radiation damage prediction method implemented by the first embodiment of the present invention to serve as a method adopted in fabrication of a silicon gate.

The following description explains processing carried out to predict a distribution of damages in an etching fabrication process of a silicon gate in accordance with the first typical example of the ion radiation damage prediction method according to the first embodiment of the present invention. The technique adopted in the prediction processing is referred to as a second typical example of the ion radiation damage prediction method according to the first embodiment of the present invention. FIG. 9 shows a flowchart representing a typical computation algorithm used for predicting a distribution of damages in an etching fabrication process of a silicon gate in accordance with the second typical example of the ion radiation damage prediction method.

The flowchart shown in FIG. 9 begins with the first step S101 at which input parameters are determined. To be more specific, this first step S101 is carried out to determine input parameters such as the type of a film serving as the subject of an etching fabrication process performed by radiating ions to the film, the pattern structure of the film, an ion flux quantity and the length of an etching time. The pattern structure of the film serving as the subject of the etching fabrication process includes the pattern size of the film and the pattern shape of the film.

Then, at the second step S102, a total incident-ion count N is determined. To put it in detail, the total incident-ion count N is the total number of incident ions hitting the film serving as the subject of the etching fabrication process within an ion radiation time period and, at the second step S102, the total incident-ion count N is determined on the basis of the input parameters in accordance with the Monte Carlo method.

Then, at the third step S103, input parameters of a sheath simulator are determined. The input parameters of a sheath simulator are the input parameters which are set at the step S20 of the flowchart shown in FIG. 8. As described earlier, the input parameters set at the step S20 of the flowchart shown in FIG. 8 include an electron density or a plasma density, an electron temperature, an ion temperature, an ion mass, a neutral-particle temperature, a neutral-particle mass, a gas pressure, a lower bias frequency, a self induction bias Vdc, a lower applied bias Vrf and a total incident-ion count.

Then, at the fourth step S104, computation is carried out by making use of the sheath simulator. In the computation carried out by using the sheath simulator, the simulator simulates the incidence of an incident ion J which has an initial energy and an angle of incidence. That is to say, the simulator simulates the behavior of the incident ion J in a sheath area. For example, the incidence energy and the incidence angle of the incident ion J entering to the film serving as the subject of the etching fabrication process are found where reference symbol J indicates that the ion is the Jth incident ion.

Then, the fifth step S105 is carried out as a step of computing the collision position of an incident ion J hitting a fabricated object and the incidence angle of the incident ion J by considering a transport path traced by the incident ion J and by adoption of the Monte Carlo method. At this fourth S105, the transport locus traced by an incident ion J as a locus to a fabricated object is found for the shape of the fabricated object by adoption of the Monte Carlo method. For example, the fifth step S105 is carried out in order to compute the position of collision between the incident ion J and the surface of the fabricated object as well as the incidence angle formed by the transport path of the incident ion J in conjunction with the surface of the fabricated object.

In addition, for incidence of every ion having an incidence energy E and an incidence angle $\phi$ at the surface of the fabricated object, data such as a crystalline defect D, an ion reflection probability P and a weight value F is computed in advance. It is to be noted that each of the crystalline defect D and the weight value F is a function of z where reference symbol z denotes the depth of the ion penetration. The above data has been computed by making use of a simulator according to classical molecular dynamics or the first principle of molecular dynamics typically for a fabricated object having a planar shape. Then, results of the computation are stored as a database in advance. That is to say, the results of the computation are typically used for creating a database as shown in conceptual diagrams of FIG. 4.

Next, the sixth step S106 is carried out to determine whether the incident ion J experiences penetration or reflection in accordance with a result of comparing a reflection probability P with a random number $\xi$. That is to say, at the sixth step S106, the reflection probability P found by referring to the incidence energy E and the incidence angle $\phi$ of the incident ion J is compared with the random number $\xi$ in order to determine whether the incident ion J penetrates into the fabricated object or the incident ion J is reflected by the surface of the fabricated object on the basis of the result of the comparison.

For example, when an incident ion J collides with the side wall of a pattern serving as a fabricated object or the bottom of the pattern, a random number $\xi$ having a value in the range $0<\xi<1$ is generated at that point. In addition, the incidence energy E and the incidence angle $\phi$ of the incident ion J are retrieved from a database and used in a spline interpolation process to find a reflection probability P. Subsequently, the random number $\xi$ is compared with the reflection probability P in order to produce a result of determination as to whether the incident ion J penetrates the portion of the pattern serving as the fabricated object to a depth z and gives rise to a crystalline defect, or the incident ion J is reflected by the surface of the pattern in a mirror-reflection phenomenon and keeps the energy of the incident ion J.

If the determination result produced at the sixth step S106 shows that the reflection probability P is smaller than the random number $\xi$, that is, the relation $\xi>P$ holds true to indicate that the incident ion J penetrates into the fabricated object, the following steps are carried out. At the seventh step S107, a database is searched for data such as the film type of the fabricated object and the type of the incident ion J. The database is used for storing a distribution of incident ions in the fabricated object. The distribution of incident ions in the fabricated object has been created in advance by calculation according to classical molecular dynamics and calculation according to the first principle of molecular dynamics on the basis of the incidence energy E of the incident ion J, the incidence angle φ of the ion and the film type of the fabricated object.

For example, for ξ>P representing a case in which a crystalline defect is generated, the database is searched for the film type of the fabricated object and the type of the incident ion J. The crystalline-defect distribution curves shown in FIG. 6A are used in a spline interpolation process to find a crystalline-defect distribution curve for an incidence energy E and an incidence angle φ as shown in the diagram of FIG. 6B. As an example, FIG. 7 is a plurality of explanatory diagrams showing a spline interpolation process for the case of an incident ion J with an incidence energy E of 200 eV and an incidence angle φ of 40 degrees.

Then, at the eighth step S108, the penetration depth of the incident ion J and the penetration location of the ion J are found. To put it in detail, at the eighth step S108, on the basis of the data found in the search operation carried out at the seventh step S107, the incidence energy E and the incidence angle φ of the incident ion J, the penetration depth of the incident ion J and the penetration location of the ion J are found.

Thus, a distribution of crystalline defects caused by an incident ion J having an incidence energy E and an incidence angle φ in a cell can be found. It is to be noted that the distribution of crystalline defects is a distribution with respect to the penetration depth z. In addition, a weighted random number is generated and used for determining the penetration depth z. It is to be noted that the weighted random number is a product of a random number and a weight F(z) representing an ion-count distribution rate at the penetration depth z where the ion-count distribution rate is the ratio of an incident-ion count to the total incident-ion count used in the calculation according to molecular dynamics.

Then, at the ninth step S109, data of defects is accumulated and an ion count ΣJ of the accumulated data of defects is compared with the total incident-ion count N in order to determine whether or not the relation ΣJ>N holds true. To put it in detail, data of defects is accumulated by storing the penetration depth z of the incident ion J and the penetration location of the ion J. In addition, the ion count ΣJ representing the number of processed incident ions J is compared with the total incident-ion count N in order to produce a result of determination as to whether or not the number of processed incident ions J has reached the total incident-ion count N.

If the determination result produced at the ninth step S109 indicates that the number of processed incident ions J has not reached the total incident-ion count N, the flow goes on to the twelfth step S112 at which the index J of the incident ion is updated by incrementing the index J by 1 as expressed by the equation J=J+1 in the flowchart shown in FIG. 9. Then, the flow goes back to the fourth step S104 in order to repeat the processing for the incident ion indicated by the updated index J (=J+1).

As a matter of fact, the sequence of steps ranging from the fourth step S104 to the ninth step S109 is carried out repeatedly till the number of processed incident ions J reaches the total incident-ion count N.

If the determination result produced at the ninth step S109 indicates that the number of processed incident ions J has reached the total incident-ion count N, on the other hand, the flow goes on to the tenth step S110 at which the ion radiation damage prediction method is terminated and a crystalline-defect distribution is created on the basis of the accumulated data of the crystalline defects.

In addition, if the determination result produced at the sixth step S106 shows that the reflection probability P is equal to or greater than the random number ξ, that is, the relation ξ≤P holds true to indicate that the incident ion J is reflected by the surface of the fabricated object, on the other hand, the flow goes on to the eleventh step S111 at which the incident ion is determined to have experienced mirror-surface reflection and the incidence angle φ of the ion is found. That is to say, at the eleventh step S111, the incident ion is determined to have experienced a mirror-surface reflection process of reflecting the ion from the surface of the fabricated object, and the incidence angle φ of the ion is detected. Then, the flow goes back to the fifth step S105 in order to repeat the processing starting with the step.

As described above, in accordance with the algorithm, the processing starting with the fourth step S104 and ending with the twelfth step S112 is carried out repeatedly for each Jth incident ion identified by the index J having a value which satisfies the relations 1≤J≤N.

In accordance with the algorithm described above, it is thus possible to predict a distribution of damages each caused by hydrogen ions at an over etching step of a silicon-gate fabrication process making use of a resist pattern as a mask. The resist pattern used at the over etching step is a gate fabrication evaluation pattern. The structure of the resist pattern has a resist film thickness of 250 nm, a BARC (Bottom Anti Reflective Coating) film thickness of 80 nm, a silicon film thickness of 150 nm, a space of 300 nm and a line width of 100 nm. In addition, the setting cell size is 2 nm×2 nm×2 nm. The resist pattern is a pattern having a fixed shape which does not change in the course of the prediction. A database for an area having a size equal to the cell size is provided in advance. The database is created by calculation according to molecular dynamics. A typical example of the database is shown in the lower diagram of FIG. 4. The over etching step is carried out for an ion flux of $10^{16}$/s·cm and an etching time period of 10 seconds. A total incident-ion count N hitting the resist pattern having a size of 500 nm×2 nm is 1×$10^{16}$. This total number of incident ions corresponds to such an over etching step. In addition, a distribution of ion energies E and a distribution of incidence angles φ are found by making use of the sheath simulator described before under conditions described below. The distributions are used as input parameters in computation based on the algorithm, which has been explained earlier by referring to the flowchart shown in FIG. 9, as computation of a transport path in the resist pattern, and also used as input parameters in interpolation computation based on the databases. It is to be noted that the input parameters found by calculation making use of the sheath simulator are used as the parameters determined at the third step S103 of the flowchart shown in FIG. 9.

The sheath simulator is set to operate under the following typical conditions:
Electron energy: 5 eV
Ion temperature: 1,000 K
Neutral-particle temperature: 400 K
Gas pressures: 1.33 Pa, 13.3 Pa and 6.7 Pa
Plasma density: $10^{10}$/cm$^3$
Plasma electric potential: 20 V
Applied bias voltage: 200 V
Self bias voltage: −200 V
Applied bias frequency: 13.56 MHz
Ion mass: 1 amu
Neutral-particle mass: 1 amu A Windows/Cygwin OS is used as a platform for execution of code of this algorithm. However, another OS can also be used as well to serve as the platform. Typical examples of the other OS are Mac, OSX, LINUX and a UNIX-family OS. The algorithm itself is written by making use of Fortran77 even though any other language can also be used as well. Typical examples of the other language are Fortran90, Fortran95, C, C++ and JAVA. That is to say, the language for writing the algorithm is not an issue.

Figure 10:
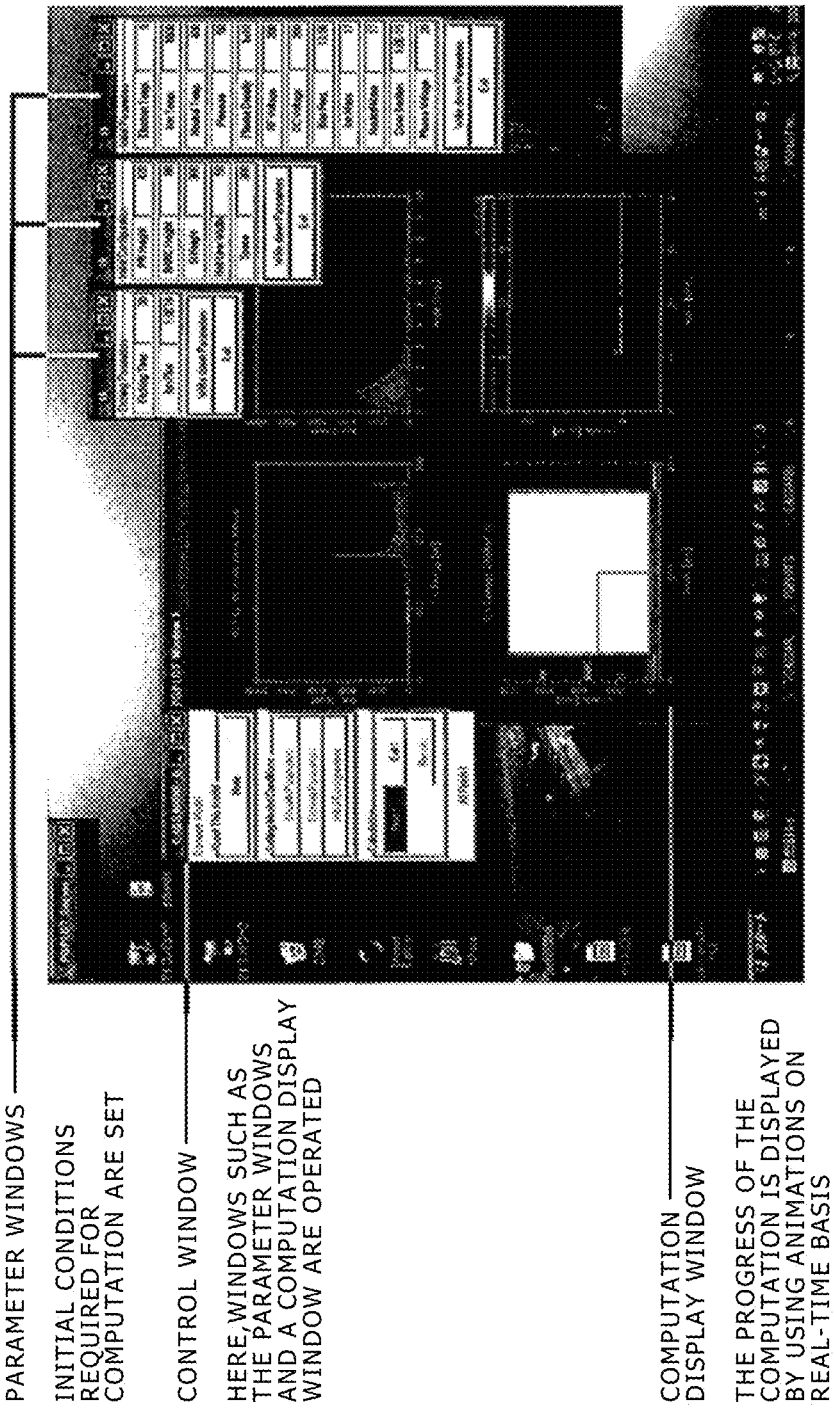
FIG. 10 is a diagram showing a rough external appearance of an ion radiation damage simulator which implements an algorithm provided by a mode of the present invention.

FIG. 10 is a diagram showing a rough external appearance of an ion radiation damage simulator which implements the algorithm. The interface section of the simulator is constructed by tcl/tk and PGPLOT. The interface section of the simulator makes computation control and computation visible to the user. However, it is also possible to use another control-system language and another tool.

Then, a 2-dimensional distribution of defects caused by ions radiated at each of gas pressures of 1.33 Pa, 13.3 Pa and 6.7 Pa is computed. In addition, a distribution of ion energies for the same conditions is also found as well. On top of that, a distribution of incidence angles each formed by the path of an ion in conjunction with the surface of the pattern is also predicted as well. By making use of the Windows/Cygwin OS as a platform which is executed in a computer having the Intel Pentium M processor with a frequency of 1.60 GHz to serve as the CPU of the computer, the computation time can be reduced to 50 hours. If only computation according to molecular dynamic is carried out, on the other hand, the time it takes to perform the computation for a sample in a planar area having a size of 2 nm×2 nm and no pattern created therein is 2,000 hours. It is thus obvious that, by adoption of the method provided by the present invention to serve as a method for predicting damages caused by radiation of ions, the computation time can be reduced substantially. It is to be noted that the computation time of 2,000 hours is the time it takes to carry out computation according to molecular dynamic for a case in which the dose quantity is set at a value equal to that for the simulator computation time of 50 hours.

In addition, according to the ion radiation damage prediction method of the present invention, a film serving as the subject of the fabrication process such as an etching fabrication process or an ion injection process does not have to be a film which is made from silicon. For example, the film can also be a film made from a silicon oxide, a film made from a silicon nitride, an organic film or another film made of a metal.

On top of that, in the method of the present invention, the shape of a pattern to which the method is applied is not an issue. That is to say, the structure of the pattern does not have to be the structure of a gate. For example, the structure of the pattern can be a side-wall structure, a shallow trench structure, a damascene structure, a contact-hole structure or a via-hole structure. In addition, the method for predicting damages caused by radiation of ions has been exemplified by describing a fixed pattern such as a pattern which serves as the subject of an over etching fabrication process. However, the method can also be applied to a pattern shape which changes with the lapse of time. A typical example of the pattern with a shape changing with time is a pattern which serves as the subject of a main etching fabrication process. On top of that, even though application of the method for predicting a 2-dimensional distribution of damages has been explained, the method can also be extended with ease to a method for predicting a 3-dimensional distribution of damages.

In addition, in order to improve the precision of the computation, an electric charging effect can be taken into consideration. The electric charging effect is an effect caused by an electric-potential difference, which is generated by electric charge accumulated on the surface of a pattern in the course of an etching fabrication process, to serve as an effect on transport loci of ions and electrons. Thus, by taking an electric charging effect into account, it is possible to recognize a transport locus of an incident ion by considering an electric-potential effect which is generated by radiation of incident ions and incident electrons to the fabricated object.

The ion radiation described above is ion radiation carried out in a plasma etching process. Thus, by adding electrical conductivities of a fabricated object to the databases created by calculation according to molecular dynamics, it is possible to compute a 2-dimensional or 3-dimensional distribution of electrical conductivities for the side wall and/or bottom of the fabricated object serving as the subject of a plasma etching process.

[Third Typical Example of the Ion Radiation Damage Prediction Method]

Figure 11:
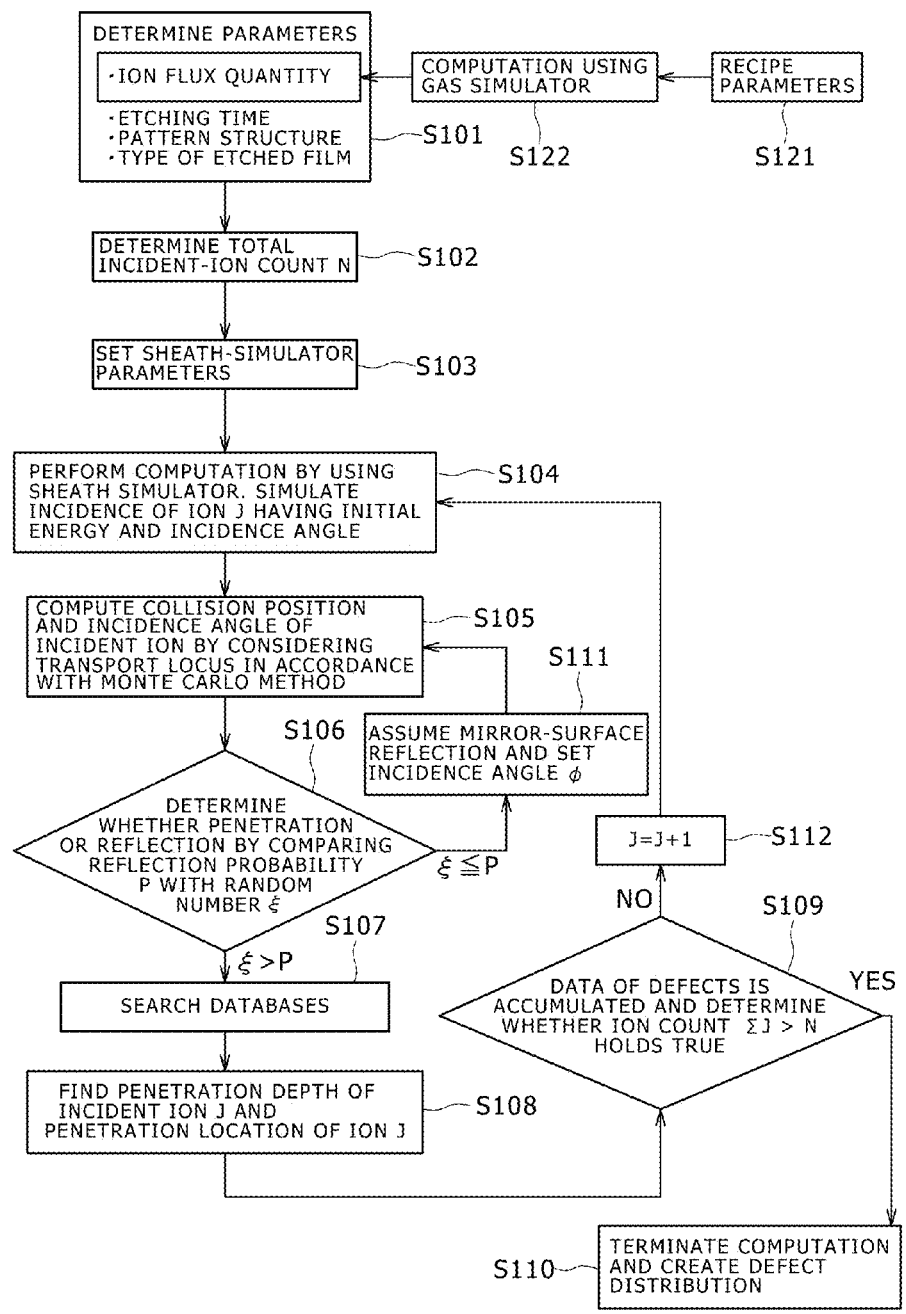
FIG. 11 shows a flowchart representing a third typical example of the ion radiation damage prediction method implemented by the first embodiment of the present invention to serve as a method adopted in fabrication of a silicon gate.

The following description explains other processing carried out to predict a distribution of damages in an etching fabrication process of a silicon gate in accordance with the first typical example of the ion radiation damage prediction method according to the first embodiment of the present invention. The technique adopted in this other processing is referred to as a third typical example of the ion radiation damage prediction method according to the first embodiment of the present invention. FIG. 11 shows a flowchart representing a typical computation algorithm used for predicting a distribution of damages in an etching fabrication process of a silicon gate in accordance with the third typical example of the ion radiation damage prediction method. The third typical example of the ion radiation damage prediction method is explained by referring to the flowchart shown in FIG. 11 as follows.

The flowchart shown in FIG. 11 begins with a first step S101 at which input parameters are determined. To be more specific, this first step S101 is carried out to determine input parameters such as the type of a film serving as the subject of an etching fabrication process performed by radiating ions to the film, the pattern structure of the film serving as the subject of the etching fabrication process, an ion flux quantity and the length of an etching time. The pattern structure of the film serving as the subject of the etching fabrication process includes the pattern size of the film and the pattern shape of the film.

In this case, the ion flux quantity is obtained as a result of calculation carried out at a step S122 which is a step of performing gas-simulator computation. The computation of the step S122 is carried out by taking a recipe parameter generated at a recipe-parameter step S121 as an input parameter. The recipe parameter is a parameter of a real-process condition.

Then, at the second step S102, a total incident-ion count N is determined. The total incident-ion count N is the total number of incident ions hitting the film serving as the subject of the etching fabrication process within an ion radiation time period. The second step S2 is carried out on the basis of the input parameters in accordance with the Monte Carlo method.

Then, at the third step S103, input parameters of a sheath simulator are determined. The input parameters of a sheath simulator at the third step S103 are the input parameters which are set at the step S20 of the flowchart shown in FIG. 8. As described earlier, the input parameters include an electron density or a plasma density, an electron temperature, an ion temperature, an ion mass, a neutral-particle temperature, a neutral-particle mass, a gas pressure, a lower bias frequency, a self induction bias Vdc, a lower applied bias Vrf and the number of incident ions.

Then, at the fourth step S104, computation is carried out by making use of the sheath simulator. In the computation is carried out by making use of the sheath simulator, the simulator simulates the incidence of an incident ion J which has an initial energy and an angle of incidence. That is to say, the simulator simulates the behavior of the incident ion J in a sheath area. For example, the incidence energy and the incidence angle of the incident ion J are found where reference symbol J appended as a suffix to the word 'ion' indicates that the ion is the Jth incident ion.

Then, the fifth step S105 is carried out as a step of computing the collision position of an incident ion J hitting a fabricated object and the incidence angle of the incident ion J by considering a transport path traced by the incident ion J by adoption of the Monte Carlo method. That is to say, the transport locus is taken into account in finding a collision position between the incident ion J and the surface of the fabricated object and an angle of incidence formed by the incident ion J in conjunction with the surface of the fabricated object. To put it in detail, at this fourth 5105, the transport locus traced by an incident ion J as a locus to a fabricated object is found for the shape of the fabricated object by adoption of the Monte Carlo method.

In addition, for incidence of every ion having an incidence energy E and an incidence angle $\phi$ at the surface of the fabricated object, data such as a crystalline defect D, an ion reflection probability P and a weight value F is computed in advance. It is to be noted that each of the crystalline defect D and the weight value F is a function of z where reference symbol z denotes the depth of the ion penetration. The data such as a crystalline defect D, an ion reflection probability P and a weight value F has been computed by making use of a simulator according to classical molecular dynamics or the first principle of molecular dynamics typically for a fabricated object having a planar shape. Then, results of the computation are stored as a database in advance. That is to say, the results of the computation are typically used for creating a database as shown in conceptual diagrams of FIG. 4.

Next, the sixth step S106 is carried out to determine whether the incident ion J experiences penetration or reflection in accordance with a result of comparing a reflection probability P with a random number $\xi$. That is to say, at the sixth step S106, the reflection probability P found by referring to the incidence energy E and the incidence angle $\phi$ of the incident ion J is compared with the random number $\xi$ in order to determine whether the incident ion J penetrates into the fabricated object or the incident ion J is reflected by the surface of the fabricated object on the basis of the result of the comparison.

For example, when an incident ion J collides with the side wall of a pattern serving as a fabricated object or the bottom of the pattern, a random number $\xi$ having a value in the range $0<\xi<1$ is generated at that point. In addition, the incidence energy E and the incidence angle $\phi$ of the incident ion J are retrieved from a database and used in a spline interpolation process to find a reflection probability P. Subsequently, the random number $\xi$ is compared with the reflection probability P in order to produce a result of determination as to whether the incident ion J penetrates the portion of the pattern serving as the fabricated object to a depth z and gives rise to a crystalline defect, or the incident ion J is reflected by the surface of the pattern in a mirror-reflection phenomenon and keeps the energy of the incident ion J.

If the determination result produced at the sixth step S106 shows that the relation $\xi>P$ holds true to indicate that the incident ion J penetrates into the fabricated object, the following steps are carried out. First of all, at the seventh step S107, a database is searched for data such as the film type of the fabricated object and the type of the incident ion J. The database is a database used for storing a distribution of incident ions in the fabricated object. The distribution of incident ions in the fabricated object has been created in advance by calculation according to classical molecular dynamics and calculation according to the first principle of molecular dynamics on the basis of the incidence energy E and the incidence angle $\phi$ of the incident ion J and the film type of the fabricated object.

For example, for $\xi>P$ representing a case in which a crystalline defect is generated, the database is searched for the film type of the fabricated object and the type of the incident ion J. The crystalline-defect distribution curves as shown in FIG. 6A are used in a spline interpolation process to find a crystalline-defect distribution curve for an incidence energy E and an incidence angle degrees as shown in the diagram of FIG. 6B. As an example, FIG. 7 is a plurality of explanatory diagrams showing a spline interpolation process for the case of an incident ion J with an incidence energy E of 200 eV and an incidence angle $\phi$ of 40 degrees.

Then, at the eighth step S108, the penetration depth of the incident ion J and the penetration location of the ion J are found. To put it in detail, at the eighth step S108, on the basis of the data found in the search operation carried out at the seventh step S107, the incidence energy E and the incidence angle $\phi$ of the incident ion J, the penetration depth of the incident ion J and the penetration location of the ion J are found.

Thus, a distribution of crystalline defects caused by an incident ion J having an incidence energy E and an incidence angle $\phi$ in a cell can be found. It is to be noted that the distribution of crystalline defects is a distribution with respect to the penetration depth z. In addition, a weighted random number is generated and used for determining the penetration depth z. It is to be noted that the weighted random number is a product of a random number and a weight F (z) representing an ion-count distribution rate at the penetration depth z where the ion-count distribution rate is the ratio of an incident-ion count to the total incident-ion count used in the calculation according to molecular dynamics.

Then, at the ninth step S109, data of defects is accumulated and an ion count $\Sigma J$ of the accumulated data of defects is compared with the incident-ion count N in order to determine whether or not the relation $\Sigma J>N$ holds true. To put it in detail, data of defects is accumulated by storing the penetration depth z of the incident ion J and the penetration location of the ion J. In addition, the ion count $\Sigma J$ representing the number of processed incident ions J is compared with the total incident-ion count N in order to produce a result of determination as to whether or not the number of processed incident ions J has reached the total incident-ion count N.

If the determination result produced at the ninth step S109 indicates that the number of processed incident ions J has not reached the total incident-ion count N, the flow goes on to the twelfth step S112 at which the index J of the incident ion is updated by incrementing the index J by 1 as expressed by the equation J=J+1 in the flowchart shown in FIG. 11. Then, the flow of the procedure of the ion radiation damage prediction method goes back to the fourth step S104 in order to repeat the processing for the incident ion indicated by the updated index J (=J+1).

As a matter of fact, the sequence of steps ranging from the fourth step S104 to the ninth step S109 is carried out repeatedly till the number of processed incident ions J reaches the total incident-ion count N.

If the determination result produced at the ninth step S109 indicates that the number of processed incident ions J has reached the total incident-ion count N, on the other hand, the flow goes on to the tenth step S110 at which the ion radiation damage prediction method is terminated and a crystalline-defect distribution is created on the basis of the accumulated data of the crystalline defects.

In addition, if the determination result produced at the sixth step S106 shows that the relation ξ≤P holds true to indicate that the incident ion J is reflected by the surface of the fabricated object, on the other hand, the flow goes on to the eleventh step S111 at which the incident ion is determined to have experienced mirror-surface reflection, and the incidence angle φ of the ion is found. That is to say, at the eleventh step S111, the incident ion is determined to have experienced a mirror-surface reflection process of reflecting the ion from the surface of the fabricated object, and the incidence angle φ of the ion is detected. Then, the flow goes back to the fifth step S105 in order to repeat the processing starting with the step.

As described above, in accordance with the algorithm, the processing starting with the fourth step S104 and ending with the twelfth step S112 is carried out repeatedly for each Jth incident ion identified by the index J having a value which satisfies the relations 1≤J≤N.

The third typical example of the method for predicting damages caused by incident ions also does not care about the type of a film serving as the subject of the etching fabrication process, the type of the structure of a pattern serving as the subject of the etching fabrication process and whether the pattern is fixed or changes with the lapse of time. In addition, the electric charging effect can also be taken into consideration.

Figure 12:
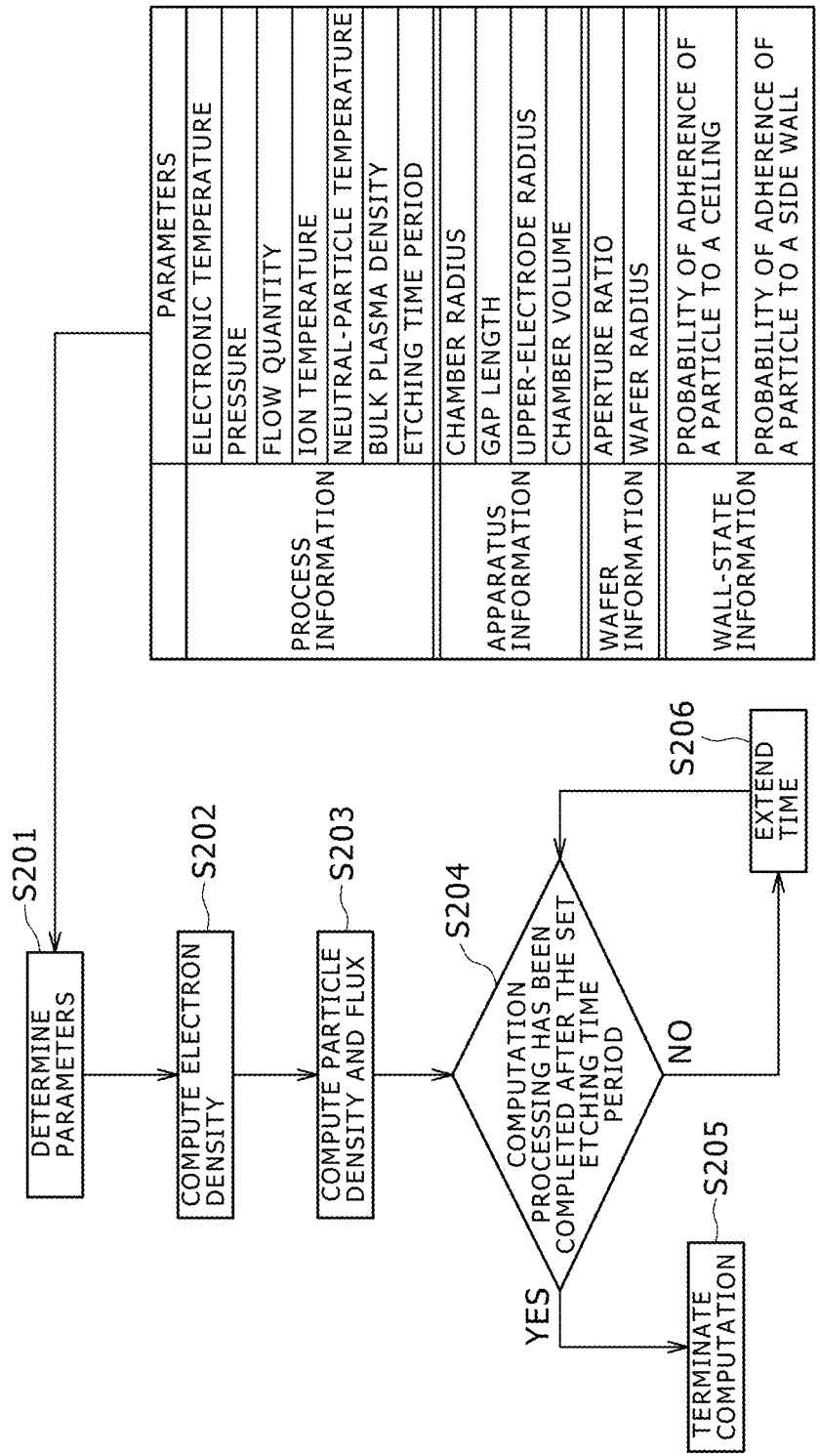
FIG. 12 shows a flowchart representing an algorithm of a gas simulator.

An algorithm adopted by a gas simulator is explained by referring to a flowchart shown in FIG. 12.

As shown in FIG. 12, the flowchart begins with a step S201 at which parameters are determined. The parameters typically include process information, apparatus information, wafer information and wall-state information which is information on chamber walls. The process information includes an electron temperature, a pressure (that is, a processing ambient temperature), a flow quantity (that is, the quantity of the flow of a process gas), an ion temperature, a neutral-particle temperature, a bulk plasma density and an etching time period. The apparatus information includes the radius of a chamber, a gap length (that is, the distance between the wafer serving as the fabrication object and an upper electrode), the radius of the upper electrode and the volume of the chamber. The wafer information includes an aperture ratio and the radius of a wafer. The wall-state information includes particle adherence probabilities such as the probability of adherence of a particle to a ceiling and the probability of adherence of a particle to a side wall.

Then, a step S202 is executed to compute an electron density. In the calculation of the electron density, for example, a value obtained from a positive glow pillar model is used. As an alternative, an actually measured value is given.

The computation of the electron density is explained as follows.

With regard to a distribution of electron densities (such as plasma densities) which are an input parameter of the model, on the assumption of the existence of a steady state and the existence of an axis-symmetrical distribution n (r) in a fluid continuity equation, a diffusion equation expressed by Eq. (3) is obtained in accordance with a positive glow pillar theory. In Eq. (3), reference notation ν denotes a collision frequency whereas reference notation D denotes a diffusion coefficient.

$$\frac{\partial^2 n}{\partial r^2} + \frac{1}{r}\frac{\partial n}{\partial r} + \frac{\nu}{D}n = 0 \qquad (3)$$

Eq. (3) is referred to as a Bessel differential equation. Given a density $n_0$ for r=0, the solution to the Bessel equation can be expressed in terms of $J_0$ as shown in Eq. 4. In Eq. (4), reference notation $J_0$ denotes a 0th-order Bessel function.

$$n = n_0 J_0(\sqrt{\nu/(D \times r)}) \qquad (4)$$

In a cylindrical side wall serving as a chamber wall, given n=0 for r=R, a minimum solution satisfying J=0 is 2.405. That is to say, the electron-density distribution n (r) is expressed in terms of the distance r from the center of the chamber and the radius Rwo of the chamber as shown in Eq. (5).

$$n = n_0 J_0(\sqrt{2.405 r/R}) \qquad (5)$$

Thus, an electron density at each position in the chamber can be found.

Then, at a step S203, a particle density and a flux are computed. The computation of the particle density and the flux is exemplified by taking a Cl (chlorine) family gas as an example. Of course, the following description of the particle density and the flux also holds true for gases other than the Cl (chlorine) family gas. For example, for the change of a radical density with time for every ion, a set of simultaneous ordinary differential equations for Cl, $Cl^+$, $Cl^{++}$, $Cl^-$, $Cl_2^+$, $SiCl_4$ and $SiCl_2$ is expressed by Eq. (6):

$$\frac{dn(i,t)}{dt} = \sum_m K_m n(i,t) n(j,t) - \frac{n(i,t)}{\tau_r} - \frac{n(i,t)}{\tau_n} \qquad (6)$$

(wherein $i = 1, \ldots, 7$)

in which, $$\frac{dn(i,t)}{dt}$$

represents density change with time,
$\Sigma_m K_m n(i,t) n(j,t)$ represents chemical reactions of m types, $$\frac{n(i,t)}{\tau_r}$$

represents emission effect, and $$\frac{n(i,t)}{\tau_n}$$

represents diffusion effect.

In Eq. (6) given above, reference symbol n (i, t) denotes the density of particles of interest, reference symbol $k_m$ denotes a chemical reaction rate, reference symbol n (j, t) denotes the density of particles serving as chemical-reaction partners of the particles of interest, reference symbol $\tau_r$ denotes an emission characteristic time and reference symbol $\tau_n$ denotes a diffusion characteristic time. The set of simultaneous ordinary differential equations expressed by Eq. (6) given above treats terms having the orders thereof much different from each other. Examples of the terms are the electron density, the chemical reaction rate and the time step. Thus, by merely adopting the ordinary 4th-order Runge-Kutta method, the solutions to the set of simultaneous ordinary differential equations may not converge in some cases. In order to solve this problem, this model adopts the Gear method which is known as an implicit numerical value solution method prepared for a set of stiff ordinary simultaneous equations. In addition, each of the electron density and the $Cl_2$ density is assumed to be a constant. This is because the time scale (the relaxation time scale) of the main chemical reaction of the plasma conversion is small (smaller than 0.1 nsec) in comparison with other chemical reactions, and a gas is always supplied.

As described above, reference symbol $\tau_r$ in the set of simultaneous ordinary differential equations represented by Eq. (6) denotes an emission characteristic time which is expressed in terms of seconds. The emission characteristic time $\tau_r$ is represented by Eq. (7) which is given below. On the right-hand side of Eq. (7), reference symbol P denotes a gas pressure expressed in terms of mT, reference symbol V denotes a chamber volume expressed in terms of liters and reference symbol Q denotes a total fluid flow expressed in terms of sccm. The emission characteristic time $\tau_r$ has a value in a range between one msec and several tens of msec.

$$\tau_r = \frac{(P/1000) \times V}{Q/79} \qquad (7)$$

In addition, also as described above, reference symbol $\tau_n$ in the set of simultaneous ordinary differential equations represented by Eq. (6) denotes a diffusion characteristic time which is expressed in terms of seconds. The diffusion characteristic time $\tau_n$ is represented by Eqs. (8) to (13) which are given below. In Eqs. (8) to (13), reference symbol $\Lambda$ denotes a characteristic diffusion length whereas reference symbol D denotes a diffusion constant. The characteristic diffusion length $\Lambda$ can be approximated by a diffusion length for a cylindrical plasma on the assumption that a plasma bulk portion is the subject of consideration. On the other hand, the diffusion constant D is a both-electrode diffusion constant. In addition, in Eqs. (8) to (13), reference symbol R denotes a chamber radius expressed in terms of cm, reference symbol $\nu$ denotes a collision frequency representing the number of collisions per second, reference symbol $k_B$ denotes the Boltzmann constant having a value of $(1.308 \times 10^{-23}$ J/K), reference symbol $T_e$ denotes an electron temperature expressed in terms of (eV×11600 K), reference symbol m denotes an ion mass expressed in terms of (Z×$1.627 \times 10^{-27}$ kg), reference symbol $n_0$ denotes a plasma density expressed in terms of $m^{-3}$ and reference symbol $\lambda_D$ denotes a Debye length expressed in terms of Debye units. The diffusion characteristic time $\sigma_n$ has a value in the order of mseconds.

$$\tau_n = \frac{\Lambda^2}{D} \qquad (8)$$

$$\frac{1}{\Lambda^2} = \left(\frac{2.405}{R}\right)^2 \qquad (9)$$

$$D = \frac{k_B T_e}{m\nu} \qquad (10)$$

$$\nu = 2.9 \times 10^{-12} n_0 \times \log Y / T_e^{1.5} \qquad (11)$$

$$Y = \frac{4\pi}{3} \lambda_D^3 \times n_e \times 9 \qquad (12)$$

$$\lambda_D = 7.43 \times 10^3 \sqrt{\frac{T_e}{n_0}} \qquad (13)$$

Then, by making use of the particle density obtained as a solution to the set of simultaneous ordinary differential equations, given a Baum velocity and a thermal motion velocity, the flux $\Gamma_{ion}$ of an ion and the flux $\Gamma_{radical}$ of a radical can be represented by respectively Eqs. (14) and (15) which are given below. In Eqs. (14) and (15), reference symbol $k_B$ denotes the Boltzmann constant, reference symbol $T_e$ denotes an electron temperature, reference symbol $T_n$ denotes a radical temperature, reference symbol $n_i$ denotes an ion density, reference symbol $n_n$ denotes a radical density, reference symbol Mi denotes the mass of an ion and reference symbol M denotes the mass of a radical.

$$\Gamma_{ion} = 0.61 \times \sqrt{\left(\frac{k_B T_e}{M_i}\right)} \times n_i \qquad (14)$$

$$\Gamma_{radical} = \frac{1}{4} \times \sqrt{\left(\frac{8 k_B T_n}{\pi M}\right)} \times n_n \qquad (15)$$

As described above, the particle density and the fluxes can be computed.

Then, a step S204 is carried out in order to determine whether or not the computation time period has lapsed. That is to say, the step S204 is carried out in order to produce a result of determination as to whether or not the set etching time period has lapsed. If the result of the determination indicates that the computation processing based on the algorithm has been completed after the set etching time period, the flow of the processing goes on to a step S205 at which the computation processing is terminated. If the result of the determination indicates that the computation processing based on the algorithm has been completed not after the set etching time period, that is, if the result of the determination indicates that the computation processing based on the algorithm has been completed within the set etching time period, on the other hand, the flow of the processing goes on to a step S206 at which extension of time is carried out in order to extend the computation processing. At the step S206, the particle density and the fluxes are computed again upon the lapse of time determined in advance. Then, the flow of the computation processing goes back to the step S204 in order to produce a result of determination as to whether or not the set etching time period has lapsed as described above. As a matter of fact, the steps S204 and S206 are carried out repeatedly till the set etching time period lapses, that is, till the determination indicates that the computation processing based on the algorithm has been completed after the set etching time period. As the result of the determination indicates that the computation processing based on the algorithm has been completed after the set etching time period, the flow of the processing goes on to the step S205 at which the computation processing is terminated.

When making use of a database created by calculation according to the first principle of molecular dynamics in the execution of the first to third typical examples of the ion radiation damage prediction method according to the first embodiment of the present invention, it is possible to add an electrical conductivity to the database like the one shown in the lower diagram of FIG. 4. By adding an electrical conductivity to the database in this way, it is possible to predict a distribution of electrical conductivities in an area damaged by the fabrication process in the course of the fabrication process and right after the fabrication process. That is to say, during and after the fabrication process, it is possible to predict electrical characteristic changes in the damaged area. A method for interpolating a value from such a database is the same as the method explained earlier by referring to the diagrams of FIG. 6.

The electrical conductivity added to a database in a process of creating the database is computed by adoption of a method based on a wave function calculated in accordance with the first principle of molecular dynamics and a method based on a non-equilibrium green function from the Hamiltonian. For more information on the methods for computing the electrical conductivities, the reader is suggested to refer to documents such as an article authored by Meir and Wingreen in the year of 1992 in Phys. Rev. Lett., Vol. 68, p. 2512.

<2. Second Embodiment>
[Typical Ion Radiation Damage Simulator]

A typical example of an ion radiation damage simulator according to a second embodiment of the present invention is explained as follows.

The typical example of the ion radiation damage simulator includes:

a processing section configured to carry out computation to predict defects generated in a fabricated object due to incident ions radiated to the fabricated object; and an output section configured to output a distribution of the defects computed by the processing section as a distribution of defects generated in the fabricated object due to incident ions radiated to the fabricated object.

The processing section carries out the computation to predict defects by adoption of any one of the computation algorithms each explained earlier as an algorithm of one of the first to third typical examples of the ion radiation damage prediction method according to the first embodiment of the present invention.

On the other hand, the output section is typically an image display apparatus for displaying a distribution of the defects computed by the processing section as a distribution of defects generated in the fabricated object due to incident ions radiated to the fabricated object. As an alternative, the output section is a printing apparatus for printing a distribution of the defects computed by the processing section as a distribution of defects generated in the fabricated object due to incident ions radiated to the fabricated object. As another alternative, the output section is typically a storage apparatus for storing a distribution of the defects computed by the processing section as a distribution of defects generated in the fabricated object due to incident ions radiated to the fabricated object. A typical example of the storage apparatus is a hard disc. By storing the distribution of defects in the storage apparatus such as a hard disc, the defect distribution can be used to feed back a process condition to a control section employed in an ion radiation apparatus which is an apparatus for radiating ions to the fabricated object.

<3. Third Embodiment>
[First Example of an Ion Radiation Apparatus]

Figure 13:
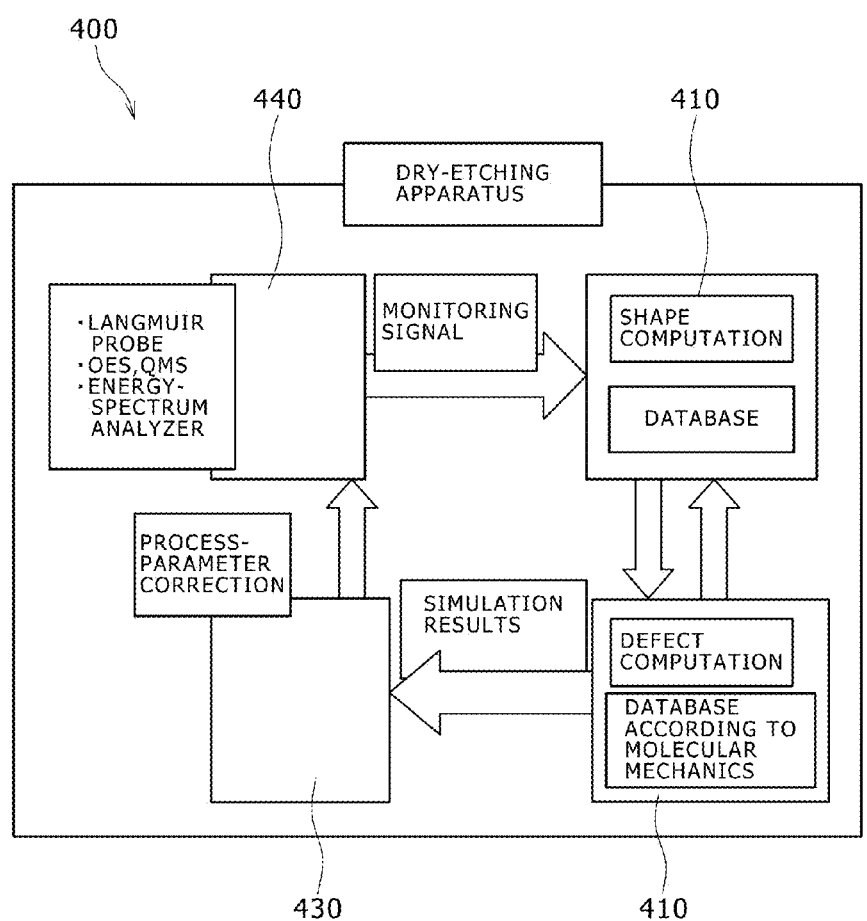
FIG. 13 is a block diagram showing a first typical example of an ion radiation apparatus according to a third embodiment of the present invention.

A first example of an ion radiation apparatus according to a third embodiment of the present invention is explained by referring to a block diagram of FIG. 13.

As shown in the block diagram of FIG. 13, the first example of the ion radiation apparatus is a dry etching apparatus 400 which employs a shape simulator 410 for predicting shape changes generated in an etching fabrication process as changes of the shape of a fabricated object serving as the subject of the etching fabrication process. In addition, the dry etching apparatus 400 also employs an ion radiation damage simulator 420 for predicting damages caused by radiation of ions in the etching fabrication process by referring to the shape changes predicted by the shape simulator 410 as shape data of the fabricated object.

On top of that, the dry etching apparatus 400 also employs a control section 430 and an etching process section 440. The control section 430 is a section configured to control an etching condition for minimizing the number of damages caused by radiation of ions on the basis of simulation results predicted by the ion radiation damage simulator 420. On the other hand, the etching process section 440 is a section configured to carry out the etching fabrication process in accordance with a command received from the control section 430.

In actuality, the etching process section 440 employs a measurement unit for monitoring the processing state. However, this measurement unit is not shown in FIG. 13. Typical examples of the measurement unit are a Langmuir probe, an OES (Optical Emission Spectroscope), a QMS (Quadrature Mass Spectroscope) and an energy spectrum analyzer.

Much like the ion radiation damage simulator according to the second embodiment described before, the ion radiation damage simulator 420 carries out computation to predict a distribution of damages by adoption of any one of the computation algorithms each explained earlier as an algorithm of one of the first to third typical examples of the ion radiation damage prediction method according to the first embodiment of the present invention.

Figure 14:
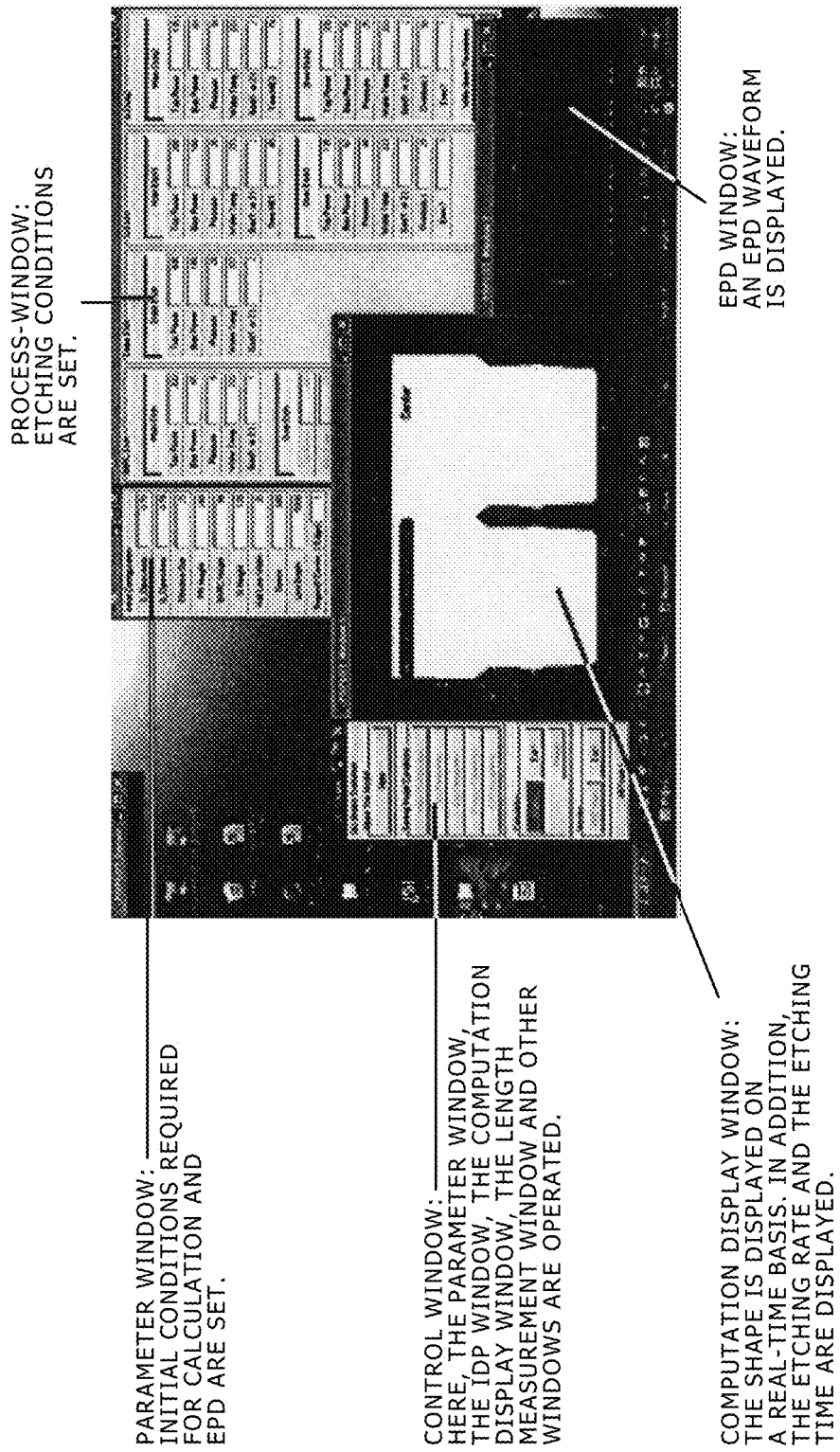
FIG. 14 is a diagram showing a rough external appearance of a shape simulator employed in the first typical example of the ion radiation apparatus according to the third embodiment.

The shape simulator 410 is a simulator for predicting a fabrication shape. FIG. 14 is a diagram showing a rough external appearance of the shape simulator 410. The shape simulator 410 and the ion radiation damage simulator 420 implement computation algorithms represented by flowcharts shown in FIGS. 15 and 16 respectively.

Figure 15:
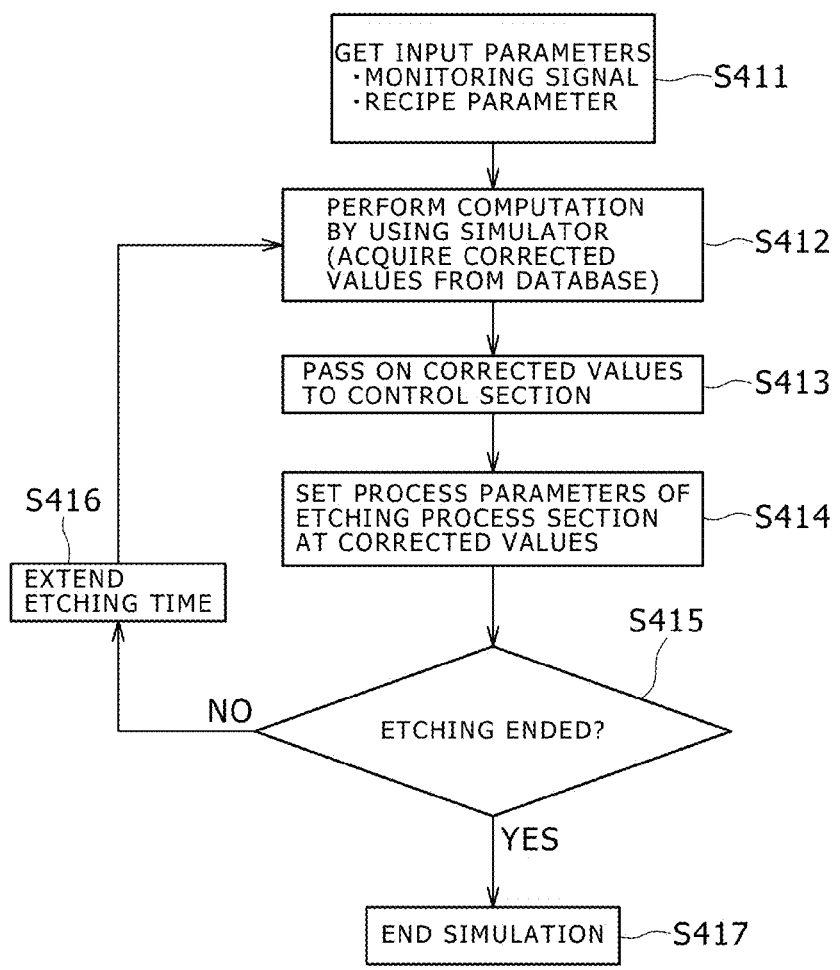
FIG. 15 shows a flowchart representing an ion radiation method adopted by the shape simulator employed in the first typical example of the ion radiation apparatus according to the third embodiment.

First of all, the following description explains the flowchart shown in FIG. 15 to serve as a flowchart representing the computation algorithm adopted by the shape simulator 410.

The flowchart shown in FIG. 15 starts with a step S411 and ends with a step S417.

The step S411 is carried out to obtain input parameters including a process recipe value and a measurement value output by a monitor employed in the etching process section 440. It is to be noted that this monitor is not shown in the block diagram of FIG. 13.

Figure 16:
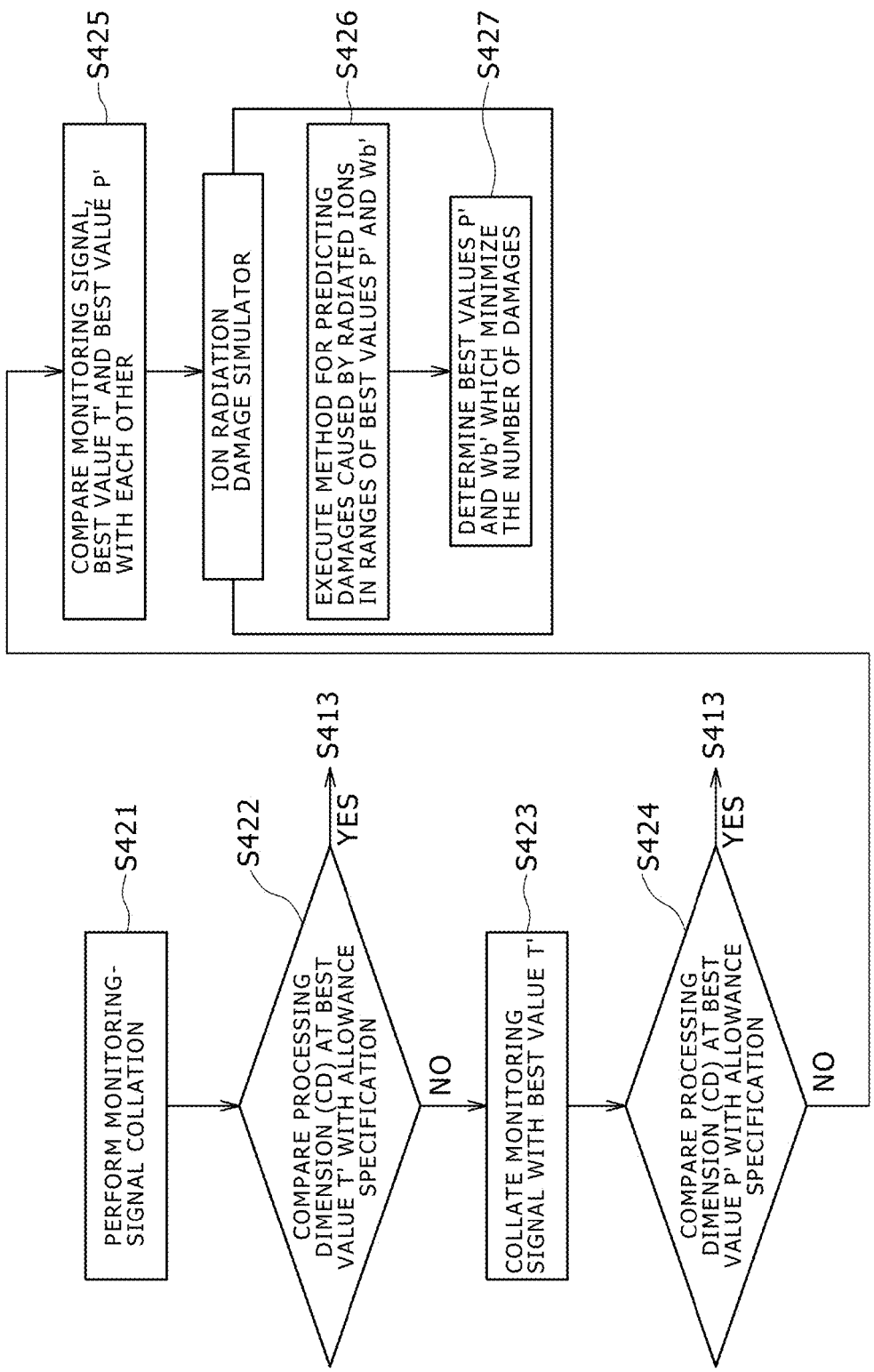
FIG. 16 shows a flowchart representing details of a computation carried out at a step S412 of the flowchart shown in FIG. 15 by making use of a simulator in order to acquire corrected values from a database.

Then, at the next step S412, the ion radiation damage simulator 420 is used to carry out calculation to obtain corrected values from a database. That is to say, the ion radiation damage simulator 420 performs an operation to acquire corrected values from a database. Details of a process carried out at the step S412 are shown in the flowchart of FIG. 16 to be described later. The database is a database used for storing data including a mask aperture ratio, a pattern structure (a solid angle), an etching gas, the type of an etched film, a wafer temperature, a gas pressure, a gas flow volume, a critical dimension (CD) of power and a taper angle.

Then, at the next step S413, the corrected values are passed on by the ion radiation damage simulator 420 to the control section 430. That is to say, the ion radiation damage simulator 420 supplies the corrected values to the control section 430. Subsequently, the control section 430 supplies the corrected values to the etching process section 440 as values at which process parameters are to be set.

Then, at the next step S414, the etching process section 440 sets process parameters at the corrected values received from the control section 430. That is to say, the etching process section 440 sets the process parameters at values based on the corrected values received from the control section 430. Subsequently, the etching fabrication process based on the parameters set at the corrected values is carried out.

Then, after time determined in advance has lapsed since the start of the etching fabrication process, the next step S415 serving as an 'etching end?' step is carried out in order to determine whether or not the etching fabrication process is to be terminated. Typically, the 'etching end?' step S415 is carried out in order to produce a result of determination as to whether or not the etching shape has attained a desired shape.

If the determination result produced at the 'etching end?' step S415 indicates that the etching fabrication process is not to be terminated yet, the flow goes on to a step S416 at which the etching time is extended. Then, the flow goes back to the step S412 at which the ion radiation damage simulator 420 obtains new corrected values based on the present etching state from the database. Subsequently, the processes of the subsequent steps S413 and S414 are repeated. As a matter of fact, the processes of the steps S416, S412, S413, S414 and S415 are carried out repeatedly till the determination result produced at the 'etching end?' step S415 indicates that the etching fabrication process is to be terminated.

As the determination result produced at the 'etching end?' step S415 indicates that the etching fabrication process is to be terminated, the flow of the computation algorithm goes on to a step S417 at which the simulation is terminated.

Next, by referring to the flowchart shown in FIG. 16, the following description explains details of the process carried out at the step S412 explained above by the ion radiation damage simulator 420 in order to obtain corrected values from the database.

The flowchart shown in FIG. 16 begins with a step S421 at which monitoring-signal collation is carried out. For example, on the basis of temperature data of a lower electrode installed in the etching process section 440, a best value T' satisfying a desired processing dimension (CD) is found by adoption of an interpolation technique.

Then, at the next step S422, the processing dimension (CD) at the best value T' is compared with an allowance specification in order to produce a result of determination as to whether or not the processing dimension (CD) at the best value T' is within an allowance specification. If the result of the determination indicates that the processing dimension (CD) at the best value T' is within the allowance specification, the flow of the processing goes on to the step S413 of the flowchart shown in FIG. 15 to pass on the corrected value to the control section 430 which then supplies the corrected value to the etching process section 440.

If the determination result produced at the next step S422 indicates that the processing dimension (CD) at the best value T' is not within the allowance specification, on the other hand, the flow of the processing goes on to a step S423 at which the monitoring signal is collated with the best value T' in order to find a best value P' satisfying a desired processing dimension (CD) by adoption of an interpolation technique typically on the basis of gas pressure data available in the etching process section 440.

Then, at the next step S424, the processing dimension (CD) at the best value P' is compared with an allowance specification in order to produce a result of determination as to whether or not the processing dimension (CD) at the best value P' is within an allowance specification. If the result of the determination indicates that the processing dimension (CD) at the best value P' is within the allowance specification, the flow goes on to the step S413 of the flowchart shown in FIG. 15 to pass on the corrected values to the control section 430 which then supplies the corrected values to the etching process section 440.

If the determination result produced at the next step S424 indicates that the processing dimension (CD) at the best value P' is not within the allowance specification, on the other hand, the flow goes on to a step S425 at which the monitoring signal, the best value T' and the best value P' are collated with each other. For example, at the step S425, a best value Wb' satisfying a desired processing dimension (CD) is found by adoption of an interpolation technique typically on the basis of lower bias power data available in the etching process section 440.

Then, at the next step S426, a method for predicting damages caused by radiation of ions in the ranges of the best values P' and Wb' is implemented by making use of an ion radiation damage simulator. The method of the step S426 is implemented in order to execute the algorithm of a first typical ion radiation damage prediction method explained earlier by referring to the flowchart shown in FIG. 1 as the first example of the ion radiation damage prediction method according to the first embodiment. It is to be noted that the method of the step S426 can also be implemented in order to execute the algorithm of a second or third typical ion radiation damage prediction method explained earlier by referring to the flowchart shown in FIG. 9 or 11 respectively as the second or third example of the ion radiation damage prediction method according to the first embodiment.

Then, at the next step S427, the best values P' and Wb' which minimize the number of damages are determined by making use of the ion radiation damage simulator. That is to say, the best values P' and Wb' determined at this step are values which minimize the number of damages.

As described above, in the dry etching apparatus 400 serving as the ion radiation apparatus provided by the present invention, an etching state in the etching process section 440 is monitored and data obtained as a result of the monitoring is supplied to the shape simulator 410. Then, shape changes generated in the shape simulator 410 as changes of the shape of the monitored object are taken into consideration in execution of processing by the ion radiation damage simulator 420 to obtain a process condition (or simulation corrected values) which minimize the number of damages caused by radiation of ions. It is to be noted that typical examples of the monitored object are a pattern serving as the subject of an etching fabrication process and a film serving as the subject of the etching fabrication process. The ion radiation damage simulator 420 supplies the simulation corrected values to the control section 430 which then gives an operation signal to the etching process section 440 in order to implement process correction.

As described above, the dry etching apparatus 400 serving as the ion radiation apparatus provided by the present invention employs the ion radiation damage simulator 420. Thus, it is possible to quantitatively predict a distribution of incident-ion penetrations into the side wall and/or bottom of a fabricated object and a 2-dimensional or 3-dimensional distribution of physical damage quantities (or crystalline defects) caused by incident ions within a realistic period of computation time. It is to be noted that, by merely carrying out experiments, it is difficult to measure the distributions within a realistic period of measurement time. It is possible to quantitatively predict the distributions within a realistic period of computation time because of the use of the databases created in advance by computation according to molecular dynamics, whereby less computation time is needed for a distribution of incident-ion penetrations and a distribution of crystalline defects.

As a result, the simulation time of an etching fabrication process carried out on the basis of radiation of ions can be shortened considerably. In addition, it is possible to minimize the number of damages caused by radiation of ions while realizing desired processing dimensions. Therefore, the ion radiation apparatus offers a merit that the TAT of the developments of a CMOS device etching process and an image sensor etching process as well as the evaluations of these processes can be shortened so that the development cost can be reduced.

[Second Example of the Ion Radiation Apparatus]

Figure 17:
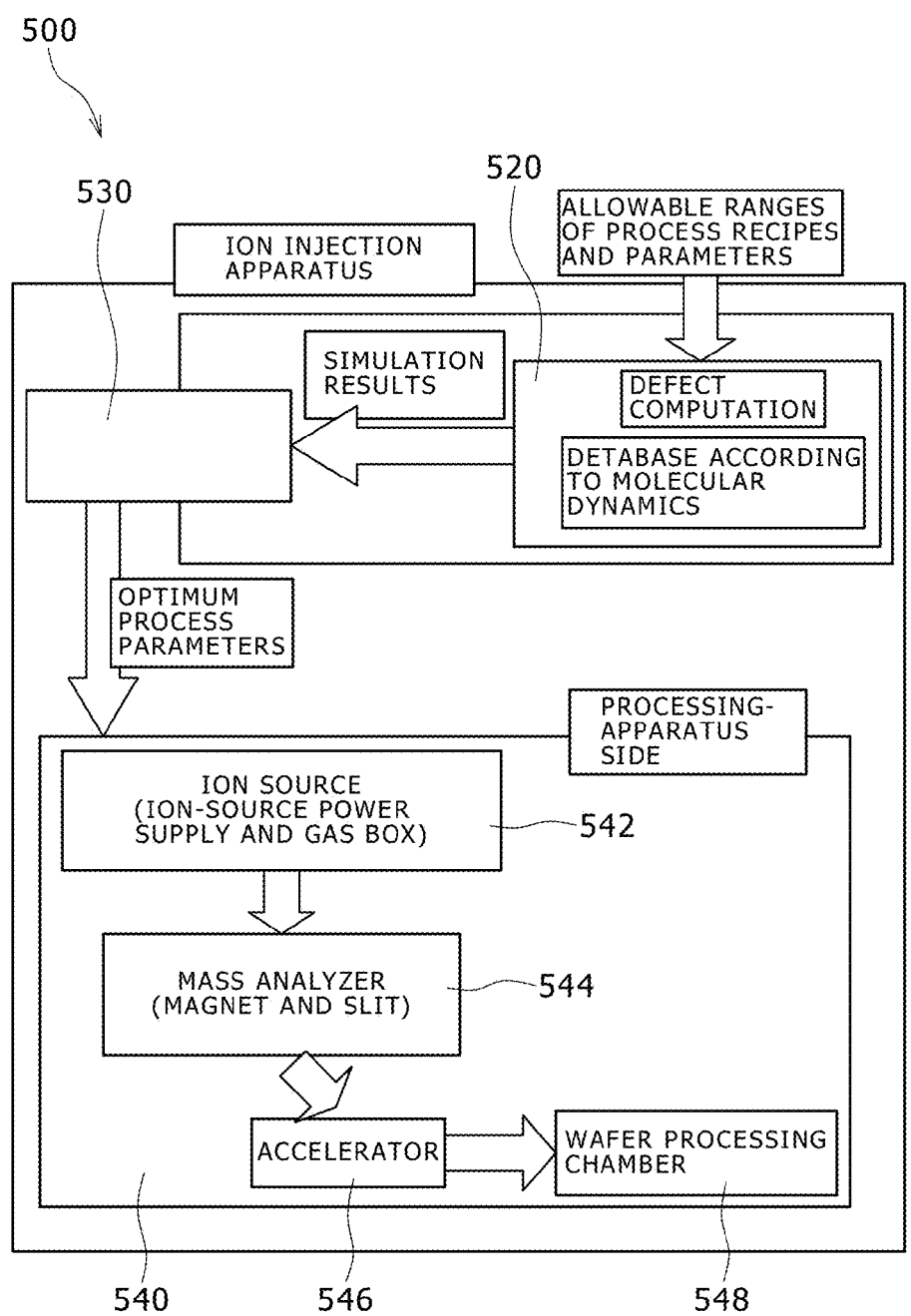
FIG. 17 is a block diagram showing a second typical example of the ion radiation apparatus according to the third embodiment of the present invention.

A second example of the ion radiation apparatus according to the third embodiment of the present invention is explained by referring to a block diagram of FIG. 17.

As shown in FIG. 17, the second example of the ion radiation apparatus is an ion injection apparatus 500 which employs an ion radiation damage simulator 520 for predicting ion radiation damages caused by injected ions.

In addition, the ion injection apparatus 500 also has a control section 530 and an ion-injection process section 540. The control section 530 is a section configured to control an injection condition for minimizing the number of damages caused by radiation of ions on the basis of simulation results predicted by the ion radiation damage simulator 520. On the other hand, the ion-injection process section 540 is a section configured to carry out an etching fabrication process in accordance with a command received from the control section 530.

The ion-injection process section 540 is provided with an ion source 542 typically including an ion-source power supply and a gas box which serves as a source for supplying a gas for injection of ions. The ion emission side of the ion source 542 is provided with a mass analysis section 544. The mass analysis section 544 has a magnet and a slit which are used to make the directions of emitted ions uniform. In addition, the ion emission side of the mass analysis section 544 is provided with an accelerator 546 for accelerating the injected ions. On top of that, the ion emission side of the accelerator 546 is provided with a wafer processing chamber 548 for radiating the accelerated ions to a wafer.

Figure 18:
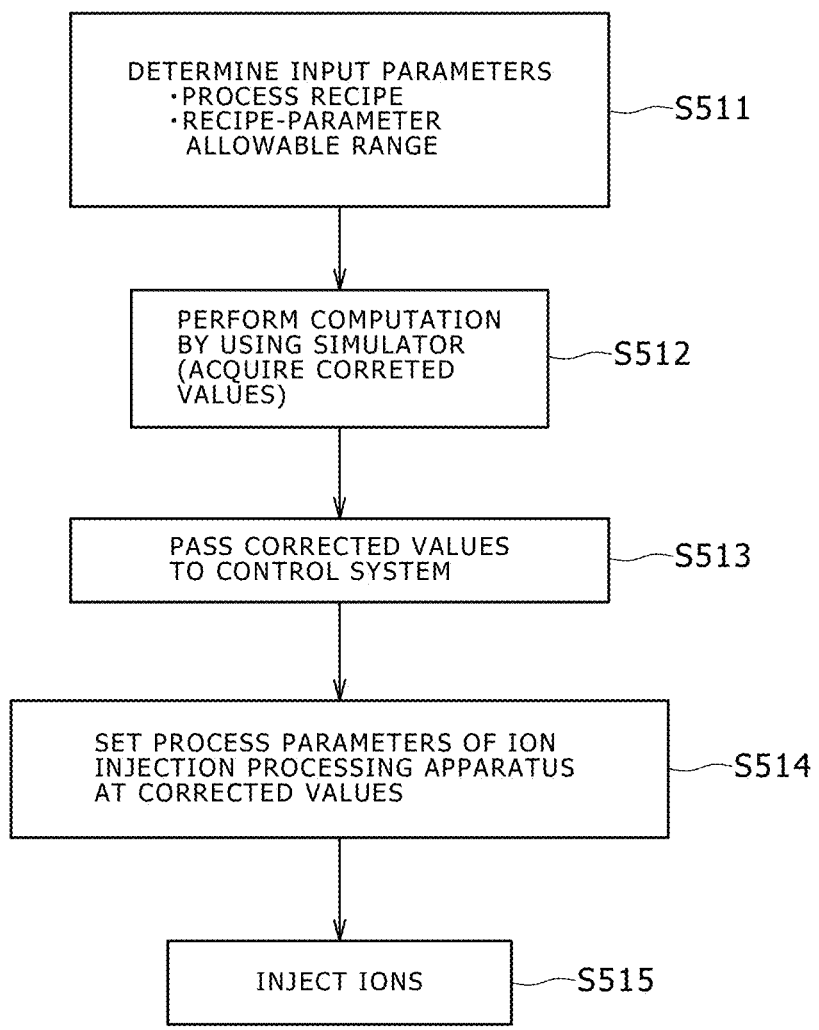
FIG. 18 shows a flowchart representing an ion radiation method adopted by the second typical example of the ion radiation apparatus according to the third embodiment.

FIG. 18 shows a flowchart representing an ion injection method which is implemented by the ion injection apparatus 500 described above.

As shown in FIG. 18, the flowchart begins with a step S511 at which input parameters are determined. To put it in detail, this step is carried out in order to set input parameters of the process condition and an allowable range of each of the parameters. Typically, the input parameters of the process condition include an ion energy, an angle of incidence and a dose quantity. The ranges of the input parameters typically includes a range of ±10% for the dose quantity and the range of the incidence angle.

Then, at the next step S512, the ion radiation damage simulator 520 carries out some computations. To put it in detail, the ion radiation damage simulator 520 carries out an operation to search a database for defect quantities in the parameter allowable range as well as interpolation on the defect quantities in order to produce an interpolated defect quantity, and performs automatic correction toward an optimum process parameter which can be used for minimizing the interpolated defect quantity. At this step, the ion radiation damage simulator 520 adopts the first typical example of the ion radiation damage prediction method. Since the radiation of ions is injection of ions in this case, it is possible to carry out the ion injection which does not have changes of the shape of the ion injection area. Thus, it is not necessary to make use of a shape simulator which is required in an etching fabrication process. It is to be noted that, in case a change of the shape of the ion injection area needs to be generated, it is possible to make use of an ion radiation damage simulator 520 which adopts the second or third typical example of the ion radiation damage prediction method. In this case, the condition used for setting the input parameters is a condition that is suitable for the ion injection.

Then, at the next step S513, the ion radiation damage simulator 520 passes on the corrected value to the control section 530. Strictly speaking, the ion radiation damage simulator 520 supplies the corrected value to the ion-injection process section 540 by way of the control section 530.

Then, at the next step S514, the ion-injection process section 540 sets the process parameter of the ion-injection process section 540 at the corrected value.

Subsequently, at the next step S515, an ion injection process is carried out. In this way, it is possible to carry out an ion injection process which suppresses the defect quantity.

In the ion injection process carried out by the ion injection apparatus 500, it is possible to further raise the ion injection energy area considering the database shown in the lower diagram of FIG. 4 to a level of the keV order. Thus, it is also possible to quantitatively predict a distribution of crystalline defects generated in the process of injecting ions to the pattern under the ion injection condition, ion injection energies for the distribution and the dependence on the ion incidence angle. As a result, it is possible to optimize the ion injection condition with the defect quantity added thereto. It is to be noted that the ion injection condition includes the ion injection energy, the ion injection angle and the dose quantity.

<4. Fourth Embodiment>

[First Typical Example of an Ion Radiation Method]

The following description explains a first typical example of an ion radiation method according to a fourth embodiment of the present invention.

The first typical example of the ion radiation method is typically adopted in the first typical example of the ion radiation apparatus.

First of all, a shape simulator is used to carry out shape simulation to predict a change caused in an etching fabrication process as a change of the shape of a fabricated object serving as the subject of the etching fabrication process.

Then, an ion radiation damage simulator is used to carry out ion radiation damage simulation to predict ion radiation damages incurred in the etching fabrication process by referring to the shape data predicted by the shape simulation as the shape data of the fabricated object.

Subsequently, an etching condition (that is, the so-called corrected value) minimizing the number of damages caused by radiation of ions is supplied to a control section. The etching condition is a condition determined on the basis of simulation results predicted by the ion radiation damage simulation.

Finally, the etching fabrication process of etching the fabricated object is carried out under a condition corrected by the control unit on the basis of the corrected value.

As the shape simulation cited above, the shape simulation explained earlier can be carried out. By the same token, as the ion radiation damage simulation mentioned above, the simulation according to the ion radiation damage simulator adopting the ion radiation damage prediction method described before can be carried out.

[Second Typical Example of the Ion Radiation Method]

The following description explains a second typical example of the ion radiation method according to the fourth embodiment of the present invention.

The second typical example of the ion radiation method is typically adopted in the second typical example of the ion radiation apparatus.

First of all, an ion radiation damage simulator is used to carry out ion radiation damage simulation to predict damages caused by ions radiated to the fabricated object.

Subsequently, on the basis of simulation results predicted in the ion radiation damage simulation, the process condition is corrected within the range of the process condition into an ion injection condition that minimizes the number of damages caused by radiation of ions.

Finally, an ion radiation process of the fabricated object is carried out under the ion injection condition.

The ion radiation damage simulator is used for carrying out the ion radiation damage simulation by adoption of the ion radiation damage prediction method described earlier.

In the ion injection process carried out in accordance with the second typical example of the ion radiation method, it is possible to further raise the ion injection energy area considering the database shown in the lower diagram of FIG. 4 to a level of the keV order. Thus, it is also possible to quantitatively predict a distribution of crystalline defects generated in the process of injecting ions to the pattern under the ion injection condition, ion injection energies for the distribution and the dependence on the ion incidence angle. As a result, it is possible to optimize the ion injection condition with the defect quantity added thereto. It is to be noted that the ion injection condition includes the ion injection energy, the ion injection angle and the dose quantity.

As described above, it is possible to quantitatively predict a distribution of incident-ion penetrations into the side wall and/or bottom of a fabricated object and a 2-dimensional or 3-dimensional distribution of physical damage quantities (or crystalline defects) caused by incident ions. It is to be noted that, by merely carrying out experiments, it is difficult to measure the distributions within a realistic period of measurement time. In addition, it is possible to quantitatively predict the distributions within a computation time period which is much shorter than that of the case of the computation according to hitherto known molecular dynamics.

On top of that, if the shape simulator is used, both the real pattern fabrication shape and the ion damage quantity can be predicted. Thus, it is possible to automatically carry out the optimization of a fabrication process which results in a desired spec shape and few damages. As a result, the ion radiation method offers a merit that the TAT of the developments of a CMOS device etching process and an image sensor etching process as well as the evaluations of these processes can be shortened so that the development cost can be reduced.

In addition, if the shape simulator is used and the electrical conductivity is taken into account, it is possible to carry out a process which takes the shape and the damages into consideration. On top of that, it is also possible even to predict a distribution of electrical conductivities existing at that time. Thus, the performance characteristics of the CMOS devices and the image sensors can be improved. The performance characteristics of the CMOS devices and the image sensors typically include the characteristic of a signal electric charge Qs, a characteristic to control a dark current and a characteristic to reduce the number of white points.

In addition, by making use of a simulator, it is possible to predict all the fabrication atmosphere gas, an ion sheath area, the shape of the fabricated object and a distribution of damages. Thus, a new structure and a new process can be developed on a table and within a short period of time without making use of an actual wafer.

In addition, the etching fabrication process and/or the ion injection process can be carried out by making use of corrected values for minimizing the number of damages. It is thus possible to decrease the number of defects which are each caused by ions radiated to the fabricated object. As a result, the device characteristics can be further improved.

The present application contains subject matter related to that disclosed in Japanese Priority Patent Application JP 2009-081098 filed in the Japan Patent Office on Mar. 30, 2009, the entire content of which is hereby incorporated by reference.

In addition, it should be understood by those skilled in the art that a variety of modifications, combinations, sub-combinations and alterations may occur, depending on design requirements and other factors as far as they are within the scope of the appended claims or the equivalents thereof.

What is claimed is:

1. A method of predicting damage of ion radiation to a fabrication object comprising:
    a first step of computing, by a processor, an incidence energy and an incidence angle of a given incident ion hitting a fabrication object;
    a second step of searching, by the processor, for data in one or more databases created in advance, wherein the databases are searched on the basis of at least the incidence energy and the incidence angle of the given incident ion, and include as data entries:
        distributions of quantities of crystalline defects affecting the fabrication object as a function of penetration depth,
        ion reflection probabilities, and
        distributions of ion penetration depths;
    a third step of computing, by the processor, a penetration depth of the given incident ion by using a distribution of ion penetration depths found by searching the databases in the second step;
    a fourth step of computing, by the processor, a penetration location of the given incident ion;
    a fifth step of computing, by the processor, a quantity of defects caused by the given incident ion by using a distribution of quantities of crystalline defects affecting the fabrication object found by searching the databases in the second step and the penetration depth computed in the third step;
    repeating the first through fifth steps for a plurality of ions and computing, by the processor, a distribution of defects caused by radiation of the plurality of ions in the fabrication object from the respective quantities of defects caused by the plurality of ions and the respective penetration locations of the plurality of incident ions.

2. The method of claim 1,
    wherein the first step further comprises:
        determining input parameters including a film type of the fabrication object, the structure of the fabrication object, an ion type, an ion flux quantity, and an ion radiation time period,
        determining, by the processor, a total incident-ion count representing the number of the plurality of incident ions hitting the fabrication object during the ion radiation time period on the basis of the Monte Carlo method and the input parameters,
    wherein, in the second step, the databases are further searched by the processor on the basis of the film type of the fabrication object and the ion type.

3. The method of claim 1,
wherein the second step further comprises determining, by the processor, whether the given incident ion penetrates into the fabrication object or is reflected by the surface of the fabrication object by comparing a reflection probability found by searching the databases in the second step with a random number, and
wherein, if it is determined in the second step that the given incident ion is reflected by the surface of the fabrication object, a second incidence angle of the given incident ion is computed by the processor and it is determined, by the processor, whether a second collision position of the given incident ion with the fabrication object exists and, if the second collision position exists, the second step is repeated with the computed second incidence angle of the given incident ion replacing the incidence angle of the given incident ion and the second collision position of the given incident ion replacing the collision position of the given incident ion.

4. The method of claim 1,
wherein, in the third step, the penetration depth of the given incident ion is computed by the processor by using a weighted random number, where the distribution of ion penetration depths found by searching the databases in the second step includes weight values representing an ion distribution rate as a function of penetration depth.

5. The method of claim 1,
wherein the ion radiation damage predicting process models a plasma etching process of etching the fabrication object;
wherein an electrical conductivity of the fabrication object is included in the databases.

6. The method of claim 1, wherein a transport path of the given incident ion is determined by the processor by considering an electric-potential effect caused by radiation of electrons generated by the radiation of incident ions to the fabrication object.

7. The method of claim 1, wherein in the first step the incidence energy and the incidence angle of the given incident ion are computed by consideration of a transport path traced by the given incident ion as a path to the fabrication object and by the Monte Carlo method taking as input parameters: a distribution of flux quantities of incident ions, a distribution of incidence energies of incident ions, and a distribution of incidence angles of incident ions,
wherein the input parameters are found by the processor by executing a gas simulation and a sheath simulation based on inputted fabrication process conditions.

8. The method of claim 1, wherein the shape of the fabrication object is fixed and does not change with the lapse of time.

9. The method of claim 1, wherein the shape of the fabrication object changes with the lapse of time.

10. The method of claim 9, wherein the shape of a portion of the fabrication object changes by radiation of the incident ions and the incident ions are radiated to the coordinate position of the portion.

11. An ion radiation method comprising:
providing a fabrication object to be a subject of an etching process;
providing a non-transitory computer readable medium having program code thereon executable by a processor to cause the processor to perform the method of claim 1;
executing, by the processor, program code for a shape simulation that predicts a change caused by the etching process as a change of the shape of the fabrication object;
determining, by the processor, from a range of values of an etching process condition, a corrected etching process condition value that allows an amount of ion-radiation damage that will be generated in the fabrication object as part of the etching process to be minimized by predicting, for each of a plurality of values of the etching process condition, respective amounts of ion-radiation damage that will be generated in the fabrication object as part of the etching process by executing the program code stored on the non-transitory computer readable medium; and
carrying out the etching process on the fabricated object in accordance with the corrected etching process condition value.

12. An ion radiation method comprising:
providing a fabrication object to be a subject of an ion-injection process;
providing a non-transitory computer readable medium having program code thereon executable by a processor to cause the processor to perform the method of claim 1;
determining, by the processor, from a range of values of an ion-injection process condition, a corrected ion-injection process condition value that allows an amount of ion-radiation damage that will be generated in the fabrication object as part of the ion-injection process to be minimized by predicting, for each of a plurality of values of the ion-injection process condition, respective amounts of ion-radiation damage that will be generated in the fabrication object as part of the ion-injection process by executing the program code stored on the non-transitory computer readable medium; and
carrying out the ion-injection process by injecting ions into the fabrication object in accordance with the corrected ion-injection process condition value.

13. An ion radiation system comprising:
a computing system including a processor and a non-transitory computer readable medium having program code thereon executable by the processor to cause the processor to perform the method of claim 1;
an etching apparatus configured to etch a fabrication object by performing an etching process the results of which depend upon at least one etching process condition that can take on any of a plurality of values,
wherein the computing system is configured to determine, by the processor, a corrected etching process condition value that allows an amount of ion-radiation damage that will be generated in the fabrication object as part of the etching process to be minimized by predicting, for each of the plurality of values of the etching process condition, respective amounts of ion-radiation damage that will be generated in the fabrication object as part of the etching process by executing the program code stored on the non-transitory computer readable medium, and
the etching apparatus is configured to carry out the etching process on the fabricated object in accordance with the corrected etching process condition value.

\* \* \* \* \*